United States Patent
Raymond et al.

(10) Patent No.: US 7,189,835 B2
(45) Date of Patent: Mar. 13, 2007

(54) PICHIA METHANOLICA SECRETORY SIGNAL

(75) Inventors: Christopher K. Raymond, Seattle, WA (US); Michael R. Stamm, Everett, WA (US)

(73) Assignee: ZymoGenetics, Inc., Seattle, WA (US)

( * ) Notice: Subject to any disclaimer, the term of this patent is extended or adjusted under 35 U.S.C. 154(b) by 69 days.

(21) Appl. No.: 11/170,268

(22) Filed: Jun. 29, 2005

(65) Prior Publication Data

US 2006/0019343 A1 Jan. 26, 2006

Related U.S. Application Data

(62) Division of application No. 10/903,350, filed on Jul. 30, 2004, now Pat. No. 6,943,234.

(60) Provisional application No. 60/501,134, filed on Sep. 8, 2003, provisional application No. 60/491,093, filed on Jul. 30, 2003.

(51) Int. Cl.
*C07H 21/04* (2006.01)
*A61K 38/00* (2006.01)

(52) U.S. Cl. .................. 536/23.1; 530/324; 530/300

(58) Field of Classification Search ................ 530/300, 530/324; 536/23.1
See application file for complete search history.

(56) References Cited

FOREIGN PATENT DOCUMENTS

EP 0495208 7/1992
WO 99/07862 2/1999

OTHER PUBLICATIONS

Anonymous, "Secondary Antibodies and Conjugates," Calbiochem Antibody Source Book, pp. 62-65, 2004, XP002315000.
Raymond et al., "Development of the Methylotrophic Yeast *Pichia methanolica* for the Expression of the 65 Kilodalton Isoform of Human Glutamate Decarboxylase," *Yeast* 14:11-23, 1998.

*Primary Examiner*—Robert A. Wax
*Assistant Examiner*—Suzanne M. Noakes
(74) *Attorney, Agent, or Firm*—Brian J. Walsh

(57) ABSTRACT

Novel *Pichia methanolica* secretory signal polypeptides, polynucleotides encoding the polypeptides, and related compositions and methods of using are disclosed. Methods of producing large amounts of recombinant proteins by employing DNA constructs having a polypeptide of interest preceded by a novel *Pichia methanolica* secretory signal sequence.

28 Claims, No Drawings

PICHIA METHANOLICA SECRETORY SIGNAL

The present application is a divisional of U.S. patent application Ser. No. 10/903,350, filed Jul. 30, 2004, now U.S. Pat. No. 6,943,234, which claims the benefit of U.S. patent application Ser. No. 60/491,093, filed Jul. 30, 2003, and 60/501,134, filed Sep. 8, 2003, all of which are herein incorporated by reference.

BACKGROUND OF THE INVENTION

Methylotrophic yeasts are those yeasts that are able to utilize methanol as a sole source of carbon and energy. Species of yeasts that have the biochemical pathways necessary for methanol utilization are classified in four genera, *Hansenula, Pichia, Candida*, and *Torulopsis*. These genera are somewhat artificial, having been based on cell morphology and growth characteristics, and do not reflect close genetic relationships (Billon-Grand, *Mycotaxon* 35:201–204, 1989; Kurtzman, *Mycologia* 84:72–76, 1992). Furthermore, not all species within these genera are capable of utilizing methanol as a source of carbon and energy. As a consequence of this classification, there are great differences in physiology and metabolism between individual species of a genus.

Methylotrophic yeasts are attractive candidates for use in recombinant protein production systems for several reasons. First, some methylotrophic yeasts have been shown to grow rapidly to high biomass on minimal defined media. Second, recombinant expression cassettes are genomically integrated and therefore mitotically stable. Third, these yeasts are capable of secreting large amounts of recombinant proteins. See, for example, Faber et al., *Yeast* 11:1331, 1995; Romanos et al., *Yeast* 8:423, 1992; Cregg et al., *Bio/Technology* 11:905, 1993; U.S. Pat. No. 4,855,242; U.S. Pat. No. 4,857,467; U.S. Pat. No. 4,879,231; and U.S. Pat. No. 4,929,555; and Raymond, U.S. Pat. Nos. 5,716,808, 5,736,383, 5,854,039, and 5,888,768.

In the commercial production of proteins via recombinant DNA technologies, it is often advantageous for the desired protein of interest to be secreted into the growth medium. Secretion of proteins from cells is generally accomplished by the presence of a short stretch of hydrophobic amino acids constituting the amino-terminal end of the translational product. This hydrophobic stretch is call the "secretory signal sequence," and it is possible to use signal sequences to effect the secretion of heterologous proteins. This is generally accomplished by the construction of an DNA construct comprising a DNA sequence encoding a secretory signal sequence, into which a gene encoding the desired heterologous protein is inserted. When such a plasmid is transformed into a host cell, the host cell will express and secrete the desired protein into the growth medium.

At present, the only mode of achieving secretion of a heterologous protein product in *Pichia methanolica* is by way of a foreign secretory signal peptide. Because foreign gene's are not native to *Pichia methanolica*, the levels of heterologous protein expression are likely suboptimal as compared to a DNA construct incorporating a secretory signal sequence native to *Pichia methanolica*.

Thus, there remains a need in the art to identify a secretory signal sequence native to *Pichia methanolica* to enable the use of methylotrophic yeasts for production of polypeptides of economic importance, including industrial enzymes and pharmaceutical proteins. The present invention provides such materials and methods as well as other, related advantages.

DETAILED DESCRIPTION OF THE INVENTION

In the description that follows, a number of terms are used extensively. The following definitions are provided to facilitate understanding of the invention.

Unless otherwise specified, "a," "an," "the," and "at least one" are used interchangeably and mean one or more than one.

The term "allelic variant" is used herein to denote an alternative form of a gene. Allelic variation is known to exist in populations and arises through mutation.

A "DNA construct" is a DNA molecule, either single- or double-stranded, that has been modified through human intervention to contain segments of DNA combined and juxtaposed in an arrangement not existing in nature.

A "DNA segment" is a portion of a larger DNA molecule having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "functionally deficient" denotes the expression in a cell of less than 10% of an activity as compared to the level of that activity in a wild-type counterpart. It is preferred that the expression level be less than 1% of the activity in the wild-type counterpart, more preferably less than 0.01% as determined by appropriate assays. It is most preferred that the activity be essentially undetectable (i.e., not significantly above background). Functional deficiencies in genes can be generated by mutations in either coding or non-coding regions.

The term "gene" is used herein to denote a DNA segment encoding a polypeptide. Where the context allows, the term includes genomic DNA (with or without intervening sequences), cDNA, and synthetic DNA. Genes may include non-coding sequences, including promoter elements.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones.

"Operably linked", when referring to DNA segments, indicates that the segments are arranged so that they function in concert for their intended purposes, e.g., transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When these terms are applied to double-stranded molecules they are used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes. Sequences within promoters that function in the initiation of transcription are often characterized by consensus nucleotide sequences. These promoter elements include RNA polymerase binding sites, TATA sequences, and transcription factor binding sites. See, in general, Watson et al., eds., *Molecular Biology of the Gene,* 4th ed., The Benjamin/Cummings Publishing Company, Inc., Menlo Park, Calif., 1987.

A "pro sequence" is a DNA sequence that commonly occurs immediately 5' to the mature coding sequence of a gene encoding a secretory protein. The pro sequence encodes a pro peptide that serves as a cis-acting chaperone as the protein moves through the secretory pathway.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are commonly defined in terms of their amino acid backbone structures; substituents such as carbohydrate groups are generally not specified, but may be present nonetheless.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway. A secretory peptide and a pro peptide may be collectively referred to as a pre-pro peptide.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., EMBO J. 4:1075 (1985); Nilsson et al., *Methods Enzymol.* 198:3 (1991)), glutathione S transferase (Smith and Johnson, *Gene* 67:31 (1988)), Glu—Glu affinity tag (Grussenmeyer et al., *Proc. Natl. Acad. Sci.* USA 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). Nucleic acid molecules encoding affinity tags are available from commercial suppliers (e.g., Pharmacia Biotech, Piscataway, N.J.).

All references cited herein are incorporated by reference in their entirety.

At present, the only mode of achieving secretion of a heterologous protein product in *Pichia methanolica* is by way of a foreign secretory signal peptide. Because foreign gene's are not native to *Pichia methanolica*, the levels of heterologous protein expression are likely suboptimal as compared to a DNA construct incorporating a secretory signal sequence native to *Pichia methanolica*. Without being limited to a theory, a native *Pichia methanolica* secretory signal peptide would increase heterologous protein production by more effectively directing transport of the heterologous protein to its target membrane, and by being cleaved more efficiently by *Pichia methanolica* peptidase on the membrane when the heterologous protein passes through it.

The present invention provides isolated DNA molecules comprising a *Pichia methanolica* secretory signal sequence, designated exo-1,3-β-glucanase gene and hereinafter referred to as "β-glucanase," is shown in SEQ ID NO:1, the encoded polypeptide is shown in SEQ ID NO:2, and the degenerate DNA molecule encoding the polypeptide of SEQ ID NO:2 is shown in SEQ ID NO:3. Those skilled in the art will recognize that SEQ ID NO:1 represents a single allele of the *P. methanolica* β-glucanase gene and that other functional alleles (allelic variants) are likely to exist, and that allelic variation may include nucleotide changes. The β-glucanase DNA sequence may be included in a DNA construct. For example, a DNA construct can include the following operably linked elements, which include a *Pichia methanolica* promoter sequence, β-glucanase DNA sequence, heterologous DNA sequence, and a *Pichia methanolica* terminator.

An *E. coli* DH10B cell culture containing an expression vector encoding *Pichia methanolica* secretory signal sequence β-glucanase was deposited with the American Type Culture Collection (10801 University Boulevard, Manassas, Va. 20110-2209) on Aug. 1, 2003, and assigned Patent Deposit Designation No. PTA-5369. This deposit will be maintained under the terms of the Budapest Treaty on the International Recognition of the Deposit of Microorganisms for the Purposes of Patent Procedure. The deposit was made merely as a convenience for those of skill in the art and is not an admission that a deposit is required under 35 U.S.C. §112.

The present invention provides polynucleotide molecules, including DNA and RNA molecules, which encode the β-glucanase polypeptides disclosed herein. Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the β-glucanase polypeptide, and fragments thereof, of SEQ ID NO:2. Those skilled in the art will recognize that the degenerate sequence of SEQ ID NO:3 also provides all RNA sequences encoding SEQ ID NO:2 by substituting U for T. Thus, β-glucanase polypeptide-encoding polynucleotides comprising nucleotide 1 to nucleotide 84 of SEQ ID NO:3 and their RNA equivalents are contemplated by the present invention. Table 1 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, with A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 2.

TABLE 2

| Amino Acid | One Letter Code | Codons | Degenerate Codon |
|---|---|---|---|
| Cys | C | TGC, TGT | TGY |
| Ser | S | AGC, AGT, TCA, TCC, TCG, TCT | WSN |
| Thr | T | ACA, ACC, ACG, ACT | ACN |
| Pro | P | CCA, CCC, CCG, CCT | CCN |
| Ala | A | GCA, GCC, GCG, GCT | GCN |
| Gly | G | GGA, GGC, GGG, GGT | GGN |
| Asn | N | AAC, AAT | AAY |
| Asp | D | GAC, GAT | GAY |
| Glu | E | GAA, GAG | GAR |
| Gln | Q | CAA, CAG | CAR |
| His | H | CAC, CAT | CAY |
| Arg | R | AGA, AGG, CGA, CGC, CGG, CGT | MGN |
| Lys | K | AAA, AAG | AAR |

TABLE 2-continued

| Amino Acid | One Letter Code | Codons | Degenerate Codon |
|---|---|---|---|
| Met | M | ATG | ATG |
| Ile | I | ATA, ATC, ATT | ATH |
| Leu | L | CTA, CTC, CTG, CTT, TTA, TTG | YTN |
| Val | V | GTA, GTC, GTG, GTT | GTN |
| Phe | F | TTC, TTT | TTY |
| Tyr | Y | TAC, TAT | TAY |
| Trp | W | TGG | TGG |
| Ter | . | TAA, TAG, TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

A full-length clone encoding β-glucanase can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to glucanase fragments, or other specific binding partners.

The present invention provides an isolated DNA molecule comprising a nucleotide sequence of SEQ ID NO:1 or complement thereof. Those skilled in the art will recognize that the sequence disclosed in SEQ ID NO:1 represents a single allele of human β-glucanase and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the β-glucanase polypeptide, are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides DNA molecules encoding a polypeptide, wherein the encoded polypeptide comprises an amino acid sequence having at least 95 percent sequence identity to SEQ ID NO:2, and wherein the encoded polypeptide is a secretory signal sequence of *Pichia methanolica*. The polypeptide may comprise, consist essentially of, or consist of SEQ ID NO:2.

The present invention also provides an isolated polypeptide comprising an amino acid sequence having at least 95 percent sequence identity with SEQ ID NO:2, wherein the polypeptide is a secretory signal sequence of *Pichia methanolica*. The polypeptide may comprise, consist essentially of, or consist of SEQ ID NO:2.

The present invention also provides isolated β-glucanase polypeptides that have a substantially similar sequence identity to the polypeptides of SEQ ID NO:2, or their orthologs. The term "substantially similar sequence identity" is used herein to denote polypeptides comprising at least 70%, at least 80%, at least 90%, at least 95%, at least 96%, at least 97%, at least 98%, at least 99%, or greater than 99% sequence identity to the sequences shown in SEQ ID NO:2, or their orthologs. The present invention also includes polypeptides that comprise an amino acid sequence having at least 70%, at least 80%, at least 90%, at least 95%, at least 96%, at least 97%, at least 98%, at least 99%, or greater than 99% sequence identity to the sequence of amino acid residues 1 to 28 of SEQ ID NO:2. The present invention further includes DNA molecules that encode such polypeptides. Methods for determining percent identity are described below.

The present invention also provides a fusion protein comprising a first portion and a second portion joined by a peptide bond, wherein the first portion comprises an amino acid sequence of SEQ ID NO:2, and the second portion comprises another polypeptide. The second portion may be a heterologous protein to *Pichia methanolica*. Optionally, a fusion protein of the present invention may further include a third portion which may include, for example, an immunoglobulin moiety comprising at least one constant region, e.g., a human immunoglobulin Fc fragment, an affinity tag, a therapeutic agent, a detectable label, and the like.

The present invention also provides an isolated DNA molecule capable of hybridizing to SEQ ID NO:1, or a complement thereof, under hybridization conditions of 0.015 M NaCl/0.0015 M sodium citrate (SSC) and about 0.1 percent sodium dodecyl sulfate (SDS) at about 50° C. to about 65° C. The nucleic acid molecule may encode at least a portion of a polypeptide, such as a functional β-glucanase of *Pichia methanolica*.

The present invention also contemplates variant β-glucanase DNA molecules that can be identified using two criteria: a determination of the similarity between the encoded polypeptide with the amino acid sequence of SEQ ID NO:2, and/or a hybridization assay, as described above. Such β-glucanase variants include nucleic acid molecules: (1) that hybridize with a nucleic acid molecule having the nucleotide sequence of SEQ ID NO:1 (or its complement) under stringent washing conditions, in which the wash stringency is equivalent to 0.5×–2×SSC with 0.1% SDS at 55–65° C.; or (2) that encode a polypeptide having at least 70%, at least 80%, at least 90%, at least 95%, at least 96%, at least 97%, at least 98%, at least 99%, or greater than 99% identity to the amino acid sequence of SEQ ID NO:2. Alternatively, β-glucanase variants can be characterized as nucleic acid molecules: (1) that hybridize with a nucleic acid molecule having the nucleotide sequence of SEQ ID NO:1 (or its complement) under highly stringent washing conditions, in which the wash stringency is equivalent to 0.1×–0.2×SSC with 0.1% SDS at 50–65° C.; and (2) that encode a polypeptide having at least 70%, at least 80%, at least 90%, at least 95%, at least 96%, at least 97%, at least 98%, at least 99%, or greater than 99% sequence identity to the amino acid sequence of SEQ ID NO:2.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes).

$$\frac{\text{Total number of identical matches}}{[\text{length of the longer sequence plus the number of gaps introduced into the longer sequence in order to align the two sequences}]} \times 100$$

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |

TABLE 3-continued

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant β-glucanase. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variant β-glucanase polypeptides or polypeptides with substantially similar sequence identity are characterized as having one or more amino acid substitutions, deletions or additions. These changes are preferably of a minor nature, that is conservative amino acid substitutions (as shown in Table 4 below) and other substitutions that do not significantly affect the folding or activity of the polypeptide; small deletions, typically of one to about 10 amino acids, preferably one to about 5 amino acids; and amino- or carboxyl-terminal extensions, such as, for instance, an amino-terminal methionine residue, a small linker peptide of up to about 5–20 residues, therapeutic agent, a detectable label, or an affinity tag. The present invention thus includes polypeptides of about 15–100 amino acid residues that comprise a sequence that is at least 70%, at least 80%, at least 90%, at least 95%, at least 96%, at least 97%, at least 98%, at least 99%, or greater than 99% identical to the corresponding region of SEQ ID NO:2. Polypeptides comprising affinity tags can further comprise a proteolytic cleavage site between the β-glucanase polypeptide and the affinity tag. Preferred such sites include thrombin cleavage sites and factor Xa cleavage sites. Polypeptides of the present invention are preferably recombinant polypeptides. In another aspect, the β-glucanase polypeptides of the present invention have at least 10, at least 15, at least 20, or at least 25 contiguous amino acids. For example, a β-glucanase polypeptide of the present invention relates to a polypeptide having at least 10, at least 15, at least 20, or at least 25 contiguous amino acids of SEQ ID NO:2.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Determination of amino acid residues that comprise regions or domains that are critical to maintaining structural integrity can be determined. Within these regions one can determine specific residues that will be more or less tolerant of change and maintain the overall tertiary structure of the molecule. Methods for analyzing sequence structure include, but are not limited to, alignment of multiple sequences with high amino acid or nucleotide identity, secondary structure propensities, binary patterns, complementary packing and buried polar interactions (Barton, *Current Opin. Struct. Biol.* 5:372–376, 1995 and Cordes et al., *Current Opin. Struct. Biol.* 6:3–10, 1996). In general, when designing modifications to molecules or identifying specific fragments determination of structure will be accompanied by evaluating activity of modified molecules.

Amino acid sequence changes are made in β-glucanase polypeptides so as to minimize disruption of higher order structure essential to biological activity. The effects of amino acid sequence changes can be predicted by, for example, computer modeling as disclosed above or determined by analysis of crystal structure (see, e.g., Lapthorn et al., *Nat.*

Struct. Biol. 2:266–268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216–226, 1992; Gray, *Protein Sci.* 2:1732–1748, 1993; and Patterson et al., *Anal. Chem.* 66:3727–3732, 1994). It is generally believed that if a modified molecule does not have the same cysteine pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205–214, 1990). Crystallography is another well known method for analyzing folding and structure. Nuclear magnetic resonance (NMR), digestive peptide mapping and epitope mapping are also known methods for analyzing folding and structurally similarities between proteins and polypeptides (Schaanan et al., *Science* 257:961–964, 1992).

A Hopp/Woods hydrophilicity profile of the β-glucanase protein sequence as shown in SEQ ID NO:2 can be generated (Hopp et al., *Proc. Natl. Acad. Sci.*, 78:3824–3828, 1981; Hopp, *J. Immun. Meth.* 88:1–18, 1986 and Triquier et al., *Protein Engineering* 11:153–169, 1998). The profile is based on a sliding six-residue window. Buried G, S, and T residues and exposed H, Y, and W residues were ignored.

Those skilled in the art will recognize that hydrophilicity or hydrophobicity will be taken into account when designing modifications in the amino acid sequence of a β-glucanase polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include Val, Leu and Ile or the group consisting of Met, Gly, Ser, Ala, Tyr and Trp residues as shown in SEQ ID NO:2. Conserved cysteine residues at positions within SEQ ID NO:2 will be relatively intolerant of substitution.

Using methods such as "FASTA" analysis described previously, regions of high similarity are identified within a family of proteins and used to analyze amino acid sequence for conserved regions. An alternative approach to identifying a variant β-glucanase polynucleotide on the basis of structure is to determine whether a nucleic acid molecule encoding a potential variant β-glucanase gene can hybridize to a nucleic acid molecule having the nucleotide sequence of SEQ ID NO:1, as discussed above.

Other methods of identifying essential amino acids in the polypeptides of the present invention are procedures known in the art, such as site-directed mutagenesis or alanine-scanning mutagenesis (Cunningham and Wells, *Science* 244: 1081 (1989), Bass et al., *Proc. Natl. Acad. Sci. USA* 88:4498 (1991), Coombs and Corey, "Site-Directed Mutagenesis and Protein Engineering," in *Proteins: Analysis and Design*, Angeletti (ed.), pages 259–311 (Academic Press, Inc. 1998)). In the latter technique, single alanine mutations are introduced at every residue in the molecule, and the resultant mutant molecules are tested for biological or biochemical activity as disclosed below to identify amino acid residues that are critical to the activity of the molecule. See also, Hilton et al., *J. Biol. Chem.* 271:4699 (1996).

The present invention also provides a fusion protein comprising a first portion and a second portion, wherein the first portion and the second portion are joined by a peptide bond, wherein the first portion comprises a functional β-glucanase, such as a polypeptide having at least 95 percent sequence identity with SEQ ID NO:2 or comprising SEQ ID NO:2, and the second portion comprises a protein of interest, such as a heterologous protein. The fusion protein may optionally comprise a third portion, such as an affinity tag, a therapeutic agent, detectable label and the like. The present invention also provides DNA molecules encoding the fusion proteins of the present invention.

The present invention also provides DNA constructs comprising the following operably linked elements: a first DNA segment comprising a transcription promoter of *Pichia methanolica*, a second DNA segment comprising a nucleotide sequence encoding a polypeptide of SEQ ID NO:2 or a polypeptide having 95 percent sequence identity with SEQ ID NO:2, a third DNA segment encoding a protein of interest, and a fourth DNA segment comprising a transcription terminator of *Pichia methanolica*. The first DNA segment may be a transcription promoter such as, for instance, glyceraldehyde-3-phosphate dehydrogenase 1 (GAP1), glyceraldehyde-3-phosphate dehydrogenase 2 (GAP2), alcohol utilization gene 1 (AUG1), alcohol utilization gene 2 (AUG2), and other *Pichia methanolica* promoters. The second DNA segment is a functional *Pichia methanolica* β-glucanse gene, e.g., SEQ ID NO:1. The third DNA segment preferably encodes a heterologous protein. The fourth DNA segment includes a *Pichia methanolica* transcription terminator, such as, for instance, GAP1, GAP2, AUG1, AUG2, and other *Pichia methanolica* terminators.

A DNA construct of the present invention may further comprise a selectable marker, e.g., ADE2 gene. In addition, a DNA construct of the present invention may further comprise a *Pichia methanolica* origin of replication or an additional origin of replication from another organism, e.g., *E. coli*, Chinese hamster overy (CHO) cells, baby hamster kidney (BHK) cells, and the like. For example, a DNA construct of the present invention can be amplified, for instance, in *E. coli* then shuttled to a host cell, such as CHO cells, for protein expression.

A DNA construct of the present invention may further include a fifth operably linked DNA segment wherein the fifth DNA segment comprises an immunoglobulin moiety comprising at least one constant region, for example, a human immunoglobulin Fc fragment, an affinity tag, a therapeutic agent and/or a detectable label.

Cultured mammalian cells are suitable hosts for DNA constructs of the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–5, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980–90, 1989; Wang and Finer, *Nature Med.* 2:714–6, 1996). The production of recombinant polypeptides in cultured mammalian cells is disclosed, for example, by Levinson et al., U.S. Pat. No. 4,713,339; Hagen et al., U.S. Pat. No. 4,784, 950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (Bangalore) 11:47–58, 1987. Transformation of insect cells and production of foreign polypeptides therein is disclosed by Guarino et al., U.S. Pat. No. 5,162,222 and WIPO publication No. WO 94/06463. Insect cells can be infected with recombinant baculovirus, commonly derived from *Autographa californica nuclear polyhedrosis virus* (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press, 1994; and, Richardson, C. D., Ed., *Baculovirus Expression Protocols. Methods in Molecular Biology*, Totowa, N J, Humana Press, 1995. The second method of making recombinant baculovirus utilizes a transposon-based system described by Luckow (Luckow, V. A, et al., *J Virol* 67:4566–79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the β-glucanase fusion protein into a baculovirus genome maintained in *E. coli* as a large plasmid called a "bacmid." The pFastBac1™ transfer vector utilizes the AcNPV polyhedrin promoter to drive the expression of the gene of interest. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971–6, 1990; Bonning, B. C. et al., *J. Gen. Virol.* 75:1551–6, 1994; and, Chazenbalk, G. D., and Rapoport, B., *J. Biol. Chem.* 270:1543–9, 1995. In such transfer vector constructs, a short or long version of the basic protein promoter can be used.

Using techniques known in the art, a transfer vector containing β-glucanase fusion protein is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g., Sf9 cells. Recombinant virus that expresses β-glucanase fusion protein is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435).

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii* and *Candida maltosa* are known in the art. See, for example, Gleeson et al., *J. Gen. Microbiol.* 132:3459–65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

Heterologous or exogenous DNA can also be introduced into *P. methanolica* cells, another useful yeast host cell, by any of several known methods, including lithium transformation (Hiep et al., *Yeast* 9:1189–1197, 1993; Tarutina and Tolstorukov, *Abst. of the 15th International Specialized Symposium on Yeasts*, Riga (USSR), 1991, 137; Ito et al., *J. Bacteriol.* 153:163, 1983; Bogdanova et al., *Yeast* 11:343, 1995), spheroplast transformation (Beggs, *Nature* 275:104, 1978; Hinnen et al., *Proc. Natl. Acad. Sci. USA* 75:1929, 1978; Cregg et al., *Mol. Cell. Biol.* 5:3376, 1985), freeze-thaw polyethylene glycol transformation (*Pichia* Expression Kit Instruction Manual, Invitrogen Corp., San Diego, Calif., Cat. No. K1710-01), or electroporation, the latter being preferred. Electroporation is the process of using a pulsed electric field to transiently permeabilize cell membranes, allowing macromolecules, such as DNA, to pass into cells. Electroporation has been described for use with mammalian (e.g., Neumann et al., *EMBO J.* 1:841–845, 1982) and fungal (e.g., Meilhoc et al., *Bio/Technology* 8:223–227, 1990) host cells. However, the actual mechanism by which DNA is transferred into the cells is not well understood. For transformation of *P. methanolica*, it has been found that electroporation is surprisingly efficient when the cells are exposed to an exponentially decaying, pulsed electric field having a field strength of from 2.5 to 4.5 kV/cm and a time constant ($\tau$) of from 1 to 40 milliseconds. The time constant $\tau$ is defined as the time required for the initial peak voltage $V_0$ to drop to a value of $V_0/e$. The time constant can be calculated as the product of the total resistance and capacitance of the pulse circuit, i.e., $\tau=R\times C$. Typically, resistance and capacitance are either preset or may be selected by the user, depending on the electroporation equipment selected. In any event, the equipment is configured in accordance with the manufacturer's instructions to provide field strength and decay parameters as disclosed above. Electroporation equipment is available from commercial suppliers (e.g., BioRad Laboratories, Hercules, Calif.).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells, for example, are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

DNA molecules for use in transforming *P. methanolica* will commonly be prepared as double-stranded, circular plasmids, which are preferably linearized prior to transformation. For polypeptide or protein production, the DNA molecules will include, in addition to the selectable marker disclosed herein, an expression cassette comprising a transcription promoter, a functional glucanase gene, a DNA segment (e.g., a cDNA) encoding the polypeptide or protein of interest, and a transcription terminator. These elements are operably linked to provide for transcription of the DNA segment of interest. It is preferred that the promoter and terminator be that of a *P. methanolica* gene. Useful promoters include those from constitutive and methanol-inducible promoters. Promoter sequences are generally contained within 1.5 kb upstream of the coding sequence of a gene, often within 1 kb or less. In general, regulated promoters are larger than constitutive promoters due the presence of regulatory elements. Methanol-inducible promoters, which include both positive and negative regulatory elements, may extend more than 1 kb upstream from the initiation ATG. Promoters are identified by function and can be cloned according to known methods.

A methanol-inducible promoter that may be used is that of a *P. methanolica* alcohol utilization gene. A representative coding strand sequence of one such gene is AUG1 (Raymond et al., U.S. Pat. No. 6,153,424). *P. methanolica* contains a second alcohol utilization gene, AUG2, the promoter of which can be used within the present invention (Raymond et al., U.S. Pat. No. 6,153,424). Other useful promoters include those of the dihydroxyacetone synthase (DHAS), formate dehydrogenase (FMD), and catalase (CAT) genes. Genes encoding these enzymes from other species have been described, and their sequences are available (e.g., Janowicz et al., *Nuc. Acids Res.* 13:2043, 1985; Hollenberg and Janowicz, EPO publication 0 299 108; Didion and Roggenkamp, *FEBS Lett.* 303:113, 1992). Genes encoding these proteins can be cloned by using the known sequences as probes, or by aligning known sequences, designing primers based on the alignment, and amplifying *P. methanolica* DNA by the polymerase chain reaction (PCR).

Constitutive promoters are those that are not activated or inactivated by environmental conditions; they are always transcriptionally active. Preferred constitutive promoters for use within the present invention include those from glyceraldehyde-3-phosphate dehydrogenase (as described herein), triose phosphate isomerase, and phosphoglycerate kinase genes of *P. methanolica*. These genes can be cloned as disclosed above or by complementation in a host cell, such as a *Saccharomyces cerevisiae* cell, having a mutation in the counterpart gene. Mutants of this type are well known in the art. See, for example, Kawasaki and Fraenkel, *Biochem. Biophys. Res. Comm.* 108:1107–1112, 1982; McKnight et al., *Cell* 46:143–147, 1986; Aguilera and Zimmermann, *Mol. Gen. Genet.* 202:83–89, 1986.

The DNA molecule of the present invention can comprise a *Pichia methanolica* glyceraldehydes-3-phosphate dehydrogenase-1 (GAPDH-1) promoter and terminator (SEQ ID NO:5) (Raymond et al., WO 00/78978), and *Pichia methanolica* glyceraldehydes-3-phosphate dehydrogenase-2 (GAPDH-2) promoter and terminator (SEQ ID NO:6) (Raymond, U.S. Pat. Nos. 6,348,331 and 6,440,720). For large scale, industrial processes where it is desirable to minimize the use of methanol, host cells may be used that have a genetic defect in a gene required for methanol utilization. Such genes include alcohol oxidase genes AUG1 and AUG2 (Zamost, B., U.S. Pat. No. 6,258,559), as well as genes encoding catalase, formaldehyde dehydrogenase, formate dehydrogenase, dihydroxyacetone synthase, dihydroxyacetone kinase, fructose 1,6-bisphosphate aldolase, and fructose 1,6-bisphosphatase. It is particularly advantageous to use cells in which both alcohol oxidase genes (AUG1 and AUG2) are deleted. Methods for producing *Pichia methanolica* strains that have a defect in AUG1, AUG2, or both AUG1 and AUG2 genes are described by Raymond et al., *Yeast* 14:11 (1998), by Raymond, U.S. Pat. No. 5,716,808, and by Raymond et al., U.S. Pat. No. 5,736,383.

The sequence of a DNA molecule comprising a *P. methanolica* glyceraldehyde-3-phosphate dehydrogenase-1 (GAPDH-1) gene promoter, coding region, and terminator is shown in SEQ ID NO:5. The gene has been designated GAP1. Those skilled in the art will recognize that SEQ ID NO:5 represents a single allele of the *P. methanolica* GAP1 gene and that other functional alleles (allelic variants) are likely to exist, and that allelic variation may include nucleotide changes in the promoter region, coding region, or terminator region.

Within SEQ ID NO:5, the GAP1 open reading frame begins with the methionine codon (ATG) at nucleotides 1733–1735. The transcription promoter is located upstream of the ATG. Gene expression experiments showed that a functional promoter was contained within the ca. 900 nucleotide 5'-flanking region of the GAP1 gene. Analysis of this promoter sequence revealed the presence of a number of sequences homologous to *Saccharomyces cerevisiae* promoter elements. These sequences include a concensus TATAAA box at nucleotides 1584 to 1591, a consensus Rap1p binding site (Graham and Chambers, *Nuc. Acids Res.* 22:124–130, 1994) at nucleotides 1355 to 1367, and potential Gcr1p binding sites (Shore, *Trends Genet.* 10:408–412, 1994) at nucleotides 1225 to 1229, 1286 to 1290, 1295 to 1299, 1313 to 1317, 1351 to 1354, 1370 to 1374, 1389 to 1393, and 1457 to 1461. While not wishing to be bound by theory, it is believed that these sequences may perform functions similar to those of their counterparts in the *S. cerevisiae* TDH3 promoter (Bitter et al., *Mol. Gen. Genet.* 231:22–32, 1991), that is, they may bind the homologous transcription regulatory elements. Mutation of the region around the consensus Gcr1p binding site in the *P. methanolica* GAP1 promoter has been found to destroy promoter activity.

Preferred portions of the sequence shown in SEQ ID NO:5 for use within the present invention as transcription promoters include segments comprising at least 900 contiguous nucleotides of the 5' non-coding region of SEQ ID NO:5, and preferably comprising nucleotide 810 to nucleotide 1724 of the sequence shown in SEQ ID NO:5. Those skilled in the art will recognize that longer portions of the 5' non-coding region of the *P. methanolica* GAP1 gene can also be used. Promoter sequences of the present invention can thus include the sequence of SEQ ID NO:5 through nucleotide 1732 in the 3' direction and can extend to or beyond nucleotide 232 in the 5' direction. For convenience and ease of manipulation, the promoter used within an expression DNA construct will generally not exceed 1.5 kb in length, and will often not exceed 1.0 kb in length.

As disclosed in more detail in the examples that follow, the sequence of SEQ ID NO:5 from nucleotide 810 to 1724 provides a functional transcription promoter. However, additional nucleotides can be removed from either or both ends of this sequence and the resulting sequence tested for promoter function by joining it to a sequence encoding a protein, preferably a protein for which a convenient assay is readily available.

Within the present invention it is preferred that the GAP1 promoter be substantially free of GAP1 gene coding sequence, which begins with nucleotide 1733 in SEQ ID NO:1. As used herein, the term "substantially free of GAP1 gene coding sequence" means that the promoter DNA includes not more than 15 nucleotides of the GAP1 coding sequences, preferably not more than 10 nucleotides, and more preferably not more than 3 nucleotides. Within one embodiment of the invention, the GAP1 promoter is provided free of coding sequence of the *P. methanolica* GAP1 gene. However, those skilled in the art will recognize that a GAP1 gene fragment that includes the initiation ATG (nucleotides 1733 to 1735) of SEQ ID NO:5 can be operably linked to a heterologous coding sequence that lacks an ATG, with the GAP1 ATG providing for initiation of translation of the heterologous sequence. Those skilled in the art will further recognize that additional GAP1 coding sequences can also be included, whereby a fusion protein comprising GAP1 and heterologous amino acid sequences is produced. Such a fusion protein may comprise a cleavage site to facilitate separation of the GAP1 and heterologous sequences subsequent to translation.

In addition to the GAP1 promoter sequence, the present invention also provides transcription terminator sequences derived from the 3' non-coding region of the *P. methanolica* GAP1 gene. A consensus transcription termination sequence (Chen and Moore, *Mol. Cell. Biol.* 12:3470–3481, 1992) is at nucleotides 2774 to 2787 of SEQ ID NO:5. Within the present invention, there are thus provided transcription terminator gene segments of at least about 60 bp in length. Longer segments, for example at least 90 bp in length or about 200 bp in length, will often be used. These segments comprise the termination sequence disclosed above, and may have as their 5' termini nucleotide 2735 of SEQ ID NO:5. Those skilled in the art will recognize, however, that the transcription terminator segment that is provided in an DNA construct can include at its 5' terminus the TAA translation termination codon at nucleotides 2732–2734 of SEQ ID NO:5 to permit the insertion of coding sequences that lack a termination codon.

The present invention also provides a DNA molecule comprising a *Pichia methanolica* glyceraldehyde-3-phosphate dehydrogenase-2 (GAPDH-2) gene promoter, coding region, and terminator as shown in SEQ ID NO:6. The gene has been designated GAP2. Those skilled in the art will recognize that SEQ ID NO:6 represents a single allele of the *P. methanolica* GAP2 gene and that other functional alleles (allelic variants) are likely to exist, and that allelic variation may include nucleotide changes in the promoter region, coding region, or terminator region.

Within SEQ ID NO:6, the GAP2 open reading frame begins with the methionine codon (ATG) at nucleotides 1093–1095. The transcription promoter is located upstream of the ATG. Gene expression experiments showed that a functional promoter was contained within the ca. 1000 nucleotide 5'-flanking region of the GAP2 gene.

Preferred portions of the sequence shown in SEQ ID NO:6 for use within the present invention as transcription promoters include segments comprising at least 900 contiguous nucleotides of the 5' non-coding region of SEQ ID NO:6, and preferably comprising nucleotide 93 to nucleotide 1080 of the sequence shown in SEQ ID NO:6. Those skilled in the art will recognize that longer portions of the 5' non-coding region of the *P. methanolica* GAP2 gene can also be used. Promoter sequences of the present invention can thus include the sequence of SEQ ID NO:6 through nucleotide 1092 in the 3' direction and can extend to or beyond nucleotide 1 in the 5' direction. In general, the promoter used within an expression DNA construct will not exceed 1.5 kb in length, and will preferably not exceed 1.0 kb in length. In addition to these promoter fragments, the invention also provides isolated DNA molecules of up to about 3300 bp, as well as isolated DNA molecules of up to 5000 bp, wherein said molecules comprise the *P. methanolica* GAP2 promoter sequence.

Within the present invention it is preferred that the GAP2 promoter be substantially free of GAP2 gene coding sequence, which begins with nucleotide 1093 in SEQ ID NO:6. As used herein, "substantially free" of GAP2 gene coding sequence means that the promoter DNA includes not more than 15 nucleotides of the GAP2 coding sequence, preferably not more than 10 nucleotides, and more preferably not more than 3 nucleotides. Within a preferred embodiment of the invention, the GAP2 promoter is provided free of coding sequence of the *P. methanolica* GAP2 gene. However, those skilled in the art will recognize that a GAP2 gene fragment that includes the initiation ATG (nucleotides 1093 to 1095) of SEQ ID NO:6 can be operably linked to a heterologous coding sequence that lacks an ATG, with the GAP2 ATG providing for initiation of translation of the heterologous sequence. Those skilled in the art will further recognize that additional GAP2 coding sequences can also be included, whereby a fusion protein comprising GAP2 and heterologous amino acid sequences is produced. Such a fusion protein may comprise a cleavage site to facilitate separation of the GAP2 and heterologous sequences subsequent to translation.

In addition to the GAP2 promoter sequence, the present invention also provides transcription terminator sequences derived from the 3' non-coding region of the *P. methanolica* GAP2 gene. A consensus transcription termination sequence (Chen and Moore, *Mol. Cell. Biol.* 12:3470–3481, 1992) is at nucleotides 2136 to 2145 of SEQ ID NO:6. Within the present invention, there are thus provided transcription terminator gene segments of at least about 50 bp, preferably at least 60 bp, more preferably at least 90 bp, still more preferably about 200 bp in length. The terminator segments of the present invention may comprise 500–1000 nucleotides of the 3' non-coding region of SEQ ID NO:6. These segments comprise the termination sequence disclosed above, and preferably have as their 5' termini nucleotide 2095 of SEQ ID NO:6. Those skilled in the art will recognize, however, that the transcription terminator segment that is provided in an expression vector can include at its 5' terminus the TAA translation termination codon at nucleotides 2092–2094 of SEQ ID NO:6 to permit the insertion of coding sequences that lack a termination codon.

A DNA construct of the present invention may further include a selectable marker. Expression vectors or DNA constructs of the present invention further comprise a selectable marker to permit identification and selection of *P. methanolica* cells containing the vector. Selectable markers provide for a growth advantage of cells containing them. The general principles of selection are well known in the art. The selectable marker is preferably a *P. methanolica* gene. Commonly used selectable markers are genes that encode enzymes required for the synthesis of amino acids or nucleotides. Cells having mutations in these genes cannot grow in media lacking the specific amino acid or nucleotide unless the mutation is complemented by the selectable marker. Use of such "selective" culture media ensures the stable maintenance of the heterologous DNA within the host cell. A selectable marker of the present invention for use in *P. methanolica* may include, for instance, a *P. methanolica* ADE2 gene, which encodes phosphoribosyl-5-aminoimidazole carboxylase (AIRC; EC 4.1.1.21). See, Raymond, U.S. Pat. No. 5,736,383. The ADE2 gene, when transformed into an ade2 host cell, allows the cell to grow in the absence of adenine. The coding strand of a representative *P. methanolica* ADE2 gene sequence is shown in SEQ ID NO:4. The sequence illustrated includes 1006 nucleotides of 5' non-coding sequence and 442 nucleotides of 3' non-coding sequence, with the initiation ATG codon at nucleotides 1007–1009. Within a preferred embodiment of the invention, a DNA segment comprising nucleotides 407–2851 is used as a selectable marker, although longer or shorter segments could be used as long as the coding portion is operably linked to promoter and terminator sequences. In the alternative, a dominant selectable marker, which provides a growth advantage to wild-type cells, may be used. Typical dominant selectable markers are genes that provide resistance to antibiotics, such as neomycin-type antibiotics (e.g., G418), hygromycin B, and bleomycin/phleomycin-type antibiotics (e.g., Zeocin™; available from Invitrogen Corporation, San Diego, Calif.). A preferred dominant selectable marker for use in *P. methanolica* is the Sh bla gene, which inhibits the activity of Zeocin™.

The present invention also provides a *Pichia methanolica* cell containing a DNA construct as described herein. The DNA construct may be genomically integrated into the *Pichia methanolica* genome with one or more copies. The *Pichia methanolica* cell may have a functionally deficient vacuolar proteinease A and/or vacuolar proteinase B. The *Pichia methanolica* cell may have a functionally deficient AUG1 and/or AUG2 gene.

The present invention also provides a method of producing a protein of interest comprising: culturing a cell of the present invention wherein the cell containing a DNA construct of the present invention wherein the third DNA segment is expressed and the protein of interest is produced, and recovering the protein of interest. Preferably, the protein of interest is heterologous or foreign to *Pichia methanolica*.

Techniques for manipulating cloned DNA molecules and introducing exogenous DNA into a variety of host cells are well known in the art and are disclosed by, for example, Sambrook et al., *Molecular Cloning: A Laboratory Manual*, 2nd ed., Cold Spring Harbor Laboratory Press, Cold Spring Harbor, N.Y., 1989; Murray, ed., Gene Transfer and Expression Protocols, Humana Press, Clifton, N.J., 1991; Glick and Pasternak, *Molecular Biotechnology: Principles and Applications of Recombinant DNA*, ASM Press, Washington, D.C., 1994; Ausubel et al. (eds.), *Short Protocols in Molecular Biology*, 3rd edition, John Wiley and Sons, Inc., NY, 1995; Wu et al., *Methods in Gene Biotechnology*, CRC Press, New York, 1997. DNA vectors, including expression vectors, commonly contain a selectable marker and origin of replication that function in a bacterial host (e.g., *E. coli*) to permit the replication and amplification of the vector in a prokaryotic host. If desired, these prokaryotic elements can be removed from a vector before it is introduced into an alternative host. For example, such prokaryotic sequences can be removed by linearization of the vector prior to its introduction into a *P. methanolica* host cell.

Within other embodiments of the invention, DNA constructs are provided that comprise a DNA segment comprising a portion of SEQ ID NO:6 that is a functional transcription terminator operably linked to a functional β-glucanase gene of the present invention, and an additional DNA segment encoding a protein of interest. Within one embodiment, the GAP2 promoter and terminator sequences of the present invention are used in combination, wherein both are operably linked to a functional β-glucanase gene and a DNA segment encoding a protein of interest within a DNA construct.

The use of *P. methanolica* cells as a host for the production of recombinant proteins is disclosed in U.S. Pat. Nos. 5,955,349, 5,888,768, 6,001,597, 5,965,389, 5,736,383, 5,854,039, 5,716,808, 5,736,383, 5,854,039, and 5,736,383. DNA constructs, e.g., expression vectors, for use in transforming *P. methanolica* will commonly be prepared as double-stranded, circular plasmids, which are preferably linearized prior to transformation. To facilitate integration of the expression vector DNA into the host chromosome, it is preferred to have the entire expression segment of the plasmid flanked at both ends by host DNA sequences (e.g., AUG1 3' sequences). Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (τ) of from 1 to 40 milliseconds, most preferably about 20 milliseconds.

Integrative transformants are preferred for use in protein production processes. Such cells can be propagated without continuous selective pressure because DNA is rarely lost from the genome. Integration of DNA into the host chromosome can be confirmed by Southern blot analysis. Briefly, transformed and untransformed host DNA is digested with restriction endonucleases, separated by electrophoresis, blotted to a support membrane, and probed with appropriate host DNA segments. Differences in the patterns of fragments seen in untransformed and transformed cells are indicative of integrative transformation. Restriction enzymes and probes can be selected to identify transforming DNA segments (e.g., promoter, terminator, heterologous DNA, and selectable marker sequences) from among the genomic fragments.

Differences in expression levels of heterologous proteins can result from such factors as the site of integration and copy number of the expression cassette among individual isolates. It is therefore advantageous to screen a number of isolates for expression level prior to selecting a production strain. Isolates exhibiting a high expression level will commonly contain multiple integrated copies of the desired expression cassette. A variety of suitable screening methods are available. For example, transformant colonies are grown on plates that are overlayed with membranes (e.g., nitrocellulose) that bind protein. Proteins are released from the cells by secretion or following lysis, and bind to the membrane. Bound protein can then be assayed using known methods, including immunoassays. More accurate analysis of expression levels can be obtained by culturing cells in liquid media and analyzing conditioned media or cell lysates, as appropriate. Methods for concentrating and purifying proteins from media and lysates will be determined in part by the protein of interest. Such methods are readily selected and practiced by the skilled practitioner.

For production of secreted proteins, host cells having functional deficiencies in the vacuolar proteases proteinase A, which is encoded by the PEP4 gene, and proteinase B, which is encoded by the PRB1 gene, are preferred in order to minimize spurious proteolysis (Raymond et al., U.S. Pat. No. 6,153,424). Vacuolar protease activity (and therefore vacuolar protease deficiency) is measured using any of several known assays. Preferred assays are those developed for *Saccharomyces cerevisiae* and disclosed by Jones, *Methods Enzymol.* 194:428–453, 1991. A preferred such assay is the APNE overlay assay, which detects activity of carboxypeptidase Y (CpY). See, Wolf and Fink, *J. Bact.* 123: 1150–1156, 1975. Because the zymogen (pro)CpY is activated by proteinase A and proteinase B, the APNE assay is indicative of vacuolar protease activity in general. The APNE overlay assay detects the carboxypeptidase Y-mediated release of β-naphthol from N-acetyl-phenylalanine-β-naphthyl-ester (APNE), which results in the formation of an isoluble red dye by the reaction of the β-naphthol with the diazonium salt Fast Garnet GBC. Cells growing on assay plates (YEPD plates are preferred) at room temperature are overlayed with 8 ml R×M. R×M is prepared by combining 0.175 g agar, 17.5 ml $H_2O$, and 5 ml 1 M Tris-HCl pH 7.4, microwaving the mixture to dissolve the agar, cooling to ~55° C., adding 2.5 ml freshly made APNE (2 mg/ml in dimethylformamide) (Sigma Chemical Co., St. Louis, Mo.), and, immediately before assay, 20 mg Fast Garnet GBC salt (Sigma Chemical Co.). The overlay is allowed to solidify, and color development is observed. Wild-type colonies are red, whereas CPY deletion strains are white. Carboxypeptidase Y activity can also be detected by the well test, in which cells are distributed into wells of a microtiter test plate and incubated in the presence of N-benzoyl-L-tyrosine p-nitroanilide (BTPNA) and dimethylformamide. The cells are permeabilized by the dimethylformamide, and CpY in the cells cleaves the amide bond in the BTPNA to give the yellow product p-nitroaniline. Assays for CpY will detect any mutation that reduces protease activity so long as that activity ultimately results in the reduction of CpY activity.

*P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine, 0.006% L-leucine).

For large-scale culture, one to two colonies of a *P. methanolica* strain can be picked from a fresh agar plate (e.g., YEPD agar) and suspended in 250 ml of YEPD broth contained in a two-liter baffled shake flask. The culture is grown for 16 to 24 hours at 30° C. and 250 rpm shaking speed. Approximately 50 to 80 milliliters of inoculum are used per liter starting fermentor volume (5–8% v/v inoculum).

A preferred fermentation medium is a soluble medium comprising glucose as a carbon source, inorganic ammonia, potassium, phosphate, iron, and citric acid. As used herein, a "soluble medium" is a medium that does not contain visible precipitation. Preferably, the medium lacks phosphate glass (sodium hexametaphosphate). A preferred medium is prepared in deionized water and does not contain calcium sulfate. As a minimal medium, it is preferred that the medium lacks polypeptides or peptides, such as yeast extracts. However, acid hydrolyzed casein (e.g., casamino acids or amicase) can be added to the medium if desired. An illustrative fermentation medium is prepared by mixing the following compounds: $(NH_4)_2SO_4$ (11.5 grams/liter), $K_2HPO_4$ (2.60 grams/liter), $KH_2PO_4$ (9.50 grams/liter), $FeSO_4.7H_2O$ (0.40 grams/liter), and citric acid (1.00 gram/liter). After adding distilled, deionized water to one liter, the solution is sterilized by autoclaving, allowed to cool, and then supplemented with the following: 60% (w/v) glucose solution (47.5 milliliters/liter), 10× trace metals solution (20.0 milliliters/liter), 1 M $MgSO_4$ (20.0 milliliters/liter), and vitamin stock solution (2.00 milliliters/liter). The 10× trace metals solution contains $FeSO_4.7H_2O$ (100 mM), $CuSO_4.5H_2O$ (2 mM), $ZnSO_4.7H_2O$ (8 mM), $MnSO_4.H_2O$ (8 mM), $CoCl_2.6H_2O$ (2 mM), $Na_2MoO_4.2H_2O$ (1 mM), $H_3BO_3$ (8 mM), KI (0.5 mM $NiSO_4.6H_2O$ (1 mM), thiamine (0.50 grams/liter), and biotin (5.00 milligrams/liter). The vitamin stock solution contains inositol (47.00 grams/liter), pantothenic acid (23.00 grams/liter), pyrodoxine (1.20 grams/liter), thiamine (5.00 grams/liter), and biotin (0.10 gram/liter). Those of skill in the art can vary these particular ingredients and amounts. For example, ammonium sulfate can be substituted with ammonium chloride, or the amount of ammonium sulfate can be varied, for example, from about 11 to about 22 grams/liter.

After addition of trace metals and vitamins, the pH of the medium is typically adjusted to pH 4.5 by addition of 10% $H_3PO_4$. Generally, about 10 milliliters/liter are added, and no additional acid addition will be required. During fermentation, the pH is maintained between about 3.5 to about 5.5, or about 4.0 to about 5.0, depending on protein produced, by addition of 5 N $NH_4OH$.

An illustrative fermentor is a BIOFLO 3000 fermentor system (New Brunswick Scientific Company, Inc.; Edison, N.J.). This fermentor system can handle either a six-liter or a fourteen-liter fermentor vessel. Fermentations performed with the six-liter vessel are prepared with three liters of medium, whereas fermentations performed with the fourteen-liter vessel are prepared with six liters of medium. The fermentor vessel operating temperature is typically set to 30° C. for the course of the fermentation, although the temperature can range between 27–31° C. depending on the protein expressed. The fermentation is initiated in a batch mode. The glucose initially present is often used by approximately 10 hours elapsed fermentation time (EFT), at which time a glucose feed can be initiated to increase the cell mass. An illustrative glucose feed contains 900 milliliters of 60% (w/v) glucose, 60 milliliters of 50% (w/v) $(NH_4)_2SO_4$, 60 milliliters of 10× trace metals solution, and 30 milliliters of 1 M $MgSO_4$. *Pichia methanolica* fermentation is robust and requires high agitation, aeration, and oxygen sparging to maintain the percentage dissolved oxygen saturation above 30%. The percentage dissolved oxygen should not drop below 15% for optimal expression and growth. The biomass typically reaches about 30 to about 80 grams dry cell weight per liter at 48 hours EFT.

Proteins produced according to the present invention are recovered from the host cells using conventional methods. Secreted proteins are recovered from the conditioned culture medium using standard methods, also selected for the particular protein. See, in general, Scopes, *Protein Purification: Principles and Practice*, Springer-Verlag, New York, 1994.

The materials and methods of the present invention can be used to produce proteins of research, industrial, or pharmaceutical interest. Such proteins include enzymes, such as lipases, cellulases, and proteases; antibodies and fragments thereof; enzyme inhibitors, including protease inhibitors; growth factors such as platelet derived growth factor (PDGF), fibroblast growth factors (FGF), epidermal growth factor (EGF), vascular endothelial growth factors (VEGFs); glutamic acid decarboxylase (GAD); cytokines, such as erythropoietin, thrombopoietin, colony stimulating factors, interleukins, and interleukin antagonist; hormones, such as insulin, proinsulin, leptin, and glucagon; adipocyte complement related proteins, such as zsig37, zsig39, zacrp8 and the like; and receptors, including growth factor receptors, which can be expressed in truncated form ("soluble receptors") or as fusion proteins with, for example, immunoglobulin constant region sequences. DNAs encoding these and other proteins are known in the art. See, for example, U.S. Pat. Nos. 4,889,919; 5,219,759; 4,868,119; 4,968,607; 4,599,311; 4,784,950; 5,792,850; 5,827,734; 4,703,008; 4,431,740; 4,762,791; 6,265,544; 6,566,499; 6,197,930; 6,482,612; and WIPO Publications WO 95/21920 and WO 96/22308.

It is particularly preferred to use the present invention to produce unglycosylated pharmaceutical proteins. Yeast cells, including *P. methanolica* cells, produce glycoproteins with carbohydrate chains that differ from their mammalian counterparts. Mammalian glycoproteins produced in yeast cells may therefore be regarded as "foreign" when introduced into a mammal, and may exhibit, for example, different pharmacokinetics than their naturally glycosylated counterparts.

The present invention also provides antibodies to polypeptides of the present invention. Antibodies to β-glucanase can be obtained, for example, using as an antigen the product of β-glucanase expression vector or β-glucanase isolated from a natural source. Particularly useful anti-β-glucanase antibodies "bind specifically" with β-glucanase. Antibodies are considered to be specifically binding if the antibodies exhibit at least one of the following two properties: (1) antibodies bind to β-glucanase with a threshold level of binding activity, and (2) antibodies do not significantly cross-react with polypeptides related to β-glucanase.

With regard to the first characteristic, antibodies specifically bind if they bind to a β-glucanase polypeptide, peptide or epitope with a binding affinity (Ka) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect β-glucanase, but not known related polypeptides using a standard Western blot analysis. Examples of known related polypeptides are orthologs and proteins from the same species that are members of a protein family.

Anti-β-glucanase antibodies can be produced using antigenic β-glucanase epitope-bearing peptides and polypeptides. Antigenic epitope-bearing peptides and polypeptides of the present invention contain a sequence of at least nine, at least 12, at least 15, at least 18, at least 21, or at least 24 to about 28 amino acids contained within SEQ ID NO:2. It is desirable that the amino acid sequence of the epitope-bearing peptide is selected to provide substantial solubility in aqueous solvents (i.e., the sequence includes relatively hydrophilic residues, while hydrophobic residues are preferably avoided). Moreover, amino acid sequences containing proline residues may be also be desirable for antibody production.

As an illustration, potential antigenic sites in β-glucanase can be identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), is first used to identify amino acid sequences representing areas of greatest local hydrophilicity (parameter: seven residues averaged). In the second step, Emini's method, Emini et al., *J. Virology* 55:836 (1985), is used to calculate surface probabilities (parameter: surface decision threshold (0.6)=1). Third, the Karplus-Schultz method, Karplus and Schultz, *Naturwissenschaften* 72:212 (1985), is used to predict backbone chain flexibility (parameter: flexibility threshold (0.2)=1). In the fourth and fifth steps of the analysis, secondary structure predictions are applied to the data using the methods of Chou-Fasman, Chou, "Prediction of Protein Structural Classes from Amino Acid Composition," in *Prediction of Protein Structure and the Principles of Protein Conformation*, Fasman (ed.), pages 549–586 (Plenum Press 1990), and Garnier-Robson, Garnier et al., *J. Mol. Biol.* 120:97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors are combined to determine a surface contour value, designated as the "antigenic index." Finally, a peak broadening function is applied to the antigenic index, which broadens major surface peaks by adding 20%, 40%, 60%, or 80% of the respective peak value to account for additional free energy derived from the mobility of surface regions relative to interior regions. This calculation is not applied, however, to any major peak that resides in a helical region, since helical regions tend to be less flexible.

Polyclonal antibodies to recombinant β-glucanase protein or to β-glucanase isolated from natural sources can be prepared using methods well-known to those of skill in the art. Antibodies can also be generated using a β-glucanase-glutathione transferase fusion protein, which is similar to a method described by Burrus and McMahon, *Exp. Cell. Res.* 220:363 (1995). General methods for producing polyclonal antibodies are described, for example, by Green et al., "Production of Polyclonal Antisera," in *Immunochemical Protocols* (Manson, ed.), pages 1–5 (Humana Press 1992), and Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995).

The immunogenicity of a β-glucanase polypeptide can be increased through the use of an adjuvant, such as alum (aluminum hydroxide) or Freund's complete or incomplete adjuvant. Polypeptides useful for immunization also include fusion polypeptides, such as fusions of β-glucanase or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horse, cow, dog, chicken, rat, mouse, rabbit, goat, guinea pig, or sheep, an anti-β-glucanase antibody of the present invention may also be derived from a subhuman primate antibody. General techniques for raising diagnostically and therapeutically useful antibodies in baboons may be found, for example, in Goldenberg et al., International Patent Publication No. WO 91/11465, and in Losman et al., *Int. J. Cancer* 46:310 (1990).

Alternatively, monoclonal anti-p-glucanase antibodies, e.g., neutralizing monoclonal antibodies to neutralize β-glucanase activity, can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology*, Vol. 1, pages 2.5.1–2.6.7 (John Wiley & Sons 1991) ["Coligan"], Picksley et al., "Production of monoclonal antibodies against proteins expressed in *E. coli*," in *DNA Cloning 2: Expression Systems, 2nd Edition*, Glover et al. (eds.), page 93 (Oxford University Press 1995)).

Briefly, monoclonal antibodies can be obtained by injecting mice with a composition comprising a β-glucanase gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology*, Vol. 10, pages 79–104 (The Humana Press, Inc. 1992)).

For particular uses, it may be desirable to prepare fragments of anti-β-glucanase antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology* Vol. 1, page 422 (Academic Press 1967), and by Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to β-glucanase polypeptide in vitro, and selecting antibody display libraries in phage or similar vectors (for instance, through use of immobilized or labeled β-glucanase protein or peptide). Genes encoding polypeptides having potential β-glucanase polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the β-glucanase sequences disclosed herein to identify proteins which bind to β-glucanase.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Polyclonal anti-idiotype antibodies can be prepared by immunizing animals with anti-β-glucanase antibodies or antibody fragments, using standard techniques. See, for example, Green et al., "Production of Polyclonal Antisera," in *Methods In Molecular Biology: Immunochemical Protocols*, Manson (ed.), pages 1–12 (Humana Press 1992). Also, see Coligan at pages 2.4.1–2.4.7. Alternatively, monoclonal anti-idiotype antibodies can be prepared using anti-β-glucanase antibodies or antibody fragments as immunogens with the techniques, described above.

Anti-idiotype β-glucanase antibodies, as well as β-glucanase polypeptides, can be used to identify and to isolate β-glucanase substrates and inhibitors. For example, proteins and peptides of the present invention can be immobilized on a column and used to bind substrate and inhibitor proteins from biological samples that are run over the column (Hermanson et al. (eds.), *Immobilized Affinity Ligand Techniques*, pages 195–202 (Academic Press 1992)). Radiolabeled or affinity labeled β-glucanase polypeptides can also be used to identify or to localize β-glucanase substrates and inhibitors in a biological sample (see, for example, Deutscher (ed.), *Methods in Enzymol.*, vol. 182, pages 721–37 (Academic Press 1990); Brunner et al., *Ann. Rev. Biochem.* 62:483 (1993); Fedan et al., *Biochem. Pharmacol.* 33:1167 (1984)).

The present invention also provides DNA molecules, such as DNA constructs containing a functional β-glucanase gene, in a kit. Alternatively, such a kit may include *Pichia methanolica* cells, such as deficient in AUG1 and/or AUG2 promoter and vacuolar proteinase A and/or vacuolar proteinase B. Moreover, the kit may include instructions on how to insert a gene encoding a protein of interest into the DNA construct as well as instructions on how to tranform the provided *Pichia methanolica* cells, and express, produce and recover the protein of interest.

The invention is further illustrated by the following nonlimiting examples.

EXAMPLES

Example 1

Identifiation of exo-1,3-β-glucanase

To clone the *P. methanolica* β-glucanase gene, a 45 kDa secreted protein was isolated from PMAD16 strain broth grown under fermentation conditions. N-terminal sequencing verified that the protein isolated was found to have 76.7% homology to the corresponding *H. polymorpha* exo-1,3-β-glucanase protein sequence and a 74.1% homology to the corresponding *S. occidentalis* exo-1,3-β-glucanase protein sequence within a 30 amino acid overlap. Degenerate sense (ZC18,176; SEQ ID NO:7 and ZC18,177; SEQ ID.NO:8) and antisense (ZC16,562; SEQ ID NO:9 and ZC16,567; SEQ ID NO:10 and ZC18,180; SEQ ID NO:11 and ZC18,181; SEQ ID NO:12) PCR primers were designed from an alignment of the coding regions of the exo-1,3-β-glucanase genes of *H. polymorpha* and *S. occidentalis*. The primers were then used to amplify *P. methanolica* genomic DNA. An amplified sequence 1280 bp long was recovered and found to have 65.0% homology to the corresponding *H. polymorpha* exo-1,3-β-glucanase protein sequence.

A *P. methanolica* genomic library was constructed in the vector pRS426 (Christianson et al., *Gene* 110:119–122, 1992), a shuttle vector comprising 2μ and *S. cerevisiae* URA3 sequences, allowing it to be propagated in *S. cerevisiae*. Genomic DNA was prepared from strain CBS6515 according to standard procedures. Briefly, cells were cultured overnight in rich media, spheroplasted with zymolyase, and lysed with SDS. DNA was precipitated from the lysate with ethanol and extracted with a phenol/chloroform mixture, then precipitated with ammonium acetate and ethanol. Gel electrophoresis of the DNA preparation showed the presence of intact, high molecular weight DNA and appreciable quantities of RNA. The DNA was partially digested with Sau 3A by incubating the DNA in the presence of a dilution series of the enzyme. Samples of the digests were analyzed by electrophoresis to determine the size distribution of fragments. DNA migrating between 4 and 12 kb was cut from the gel and extracted from the gel slice. The size-fractionated DNA was then ligated to pRS426 that had been digested with Bam HI and treated with alkaline phosphatase. Aliquots of the reaction mixture were electroporated into *E. coli* MC1061 cells using an electroporator (Gene Pulser™; BioRad Laboratories, Hercules, Calif.) as recommended by the manufacturer.

The library was screened by PCR using sense and antisense primers designed from the sequenced region of the *P. methanolica* exo-1,3-β-glucanase gene fragment. The PCR reaction mixture was incubated for one minute at 94° C.: followed by 34 cycles of 94° C., one minute, 52° C., one minute, 72° C., eleven minutes. Starting with 43 library pools, positive pools were identified and broken down to individual colonies. A single colony with a pRS426 plasmid containing the *P. methanolica* exo-1,3-β-glucanase gene as its insert was isolated. The orientation of the exo-1,3-glucanase gene and the length of the 5' and 3' flanking sequences in the insert were deduced by DNA sequencing (SEQ ID NO:1). This gene was designated exo-1,3-β-glucanase.

Example 2

Construction and Characterization of ZACRP3 Untagged Yeast Expression Vectors Utilizing a Heterologous *S. cerevisiae* Leader and an Endogenous *P. methanolica* Leader Expression of zacrp3 (Piddington et al., U.S. Pat. No. 6,521,233) in *Pichia methanolica* utilizes the expression system as described in Raymond, U.S. Pat. No. 5,888,768; Raymond, U.S. Pat. No. 5,955,349; and Raymond, U.S. Pat. No. 6,001,597. An expression plasmid containing all or part of a polynucleotide encoding zacrp3 is constructed via homologous recombination (Raymond et al., U.S. Pat. No. 5,854,039). An expression vector was built from pVRM51 to express untagged zacrp3 polypeptides. PVRM51 is a derivative of the pCZR204 expression vector; it differs from pCZR204 by one amino acid (D83→Y83) within the alpha factor prepro (αFpp) sequence to enhance Kex2p cleavage. The pVRM51 vector contains the AUG1 promoter, followed by the αFpp (D83→Y83) leader sequence and an amino-terminal peptide tag (Glu—Glu), followed by a blunt-ended Sma I restriction site, a carboxy-terminal peptide tag (Glu—Glu), a translational STOP codon, followed by the AUG1 terminator, the ADE2 selectable marker, and finally the AUG1 3' untranslated region. Also included in this vector are the URA3 and CEN-ARS sequences required for selection and replication in *S. cerevisiae*, and the AmpR and colE1 ori sequences required for selection and replication in *E. coli*. A second expression vector was built from zCZR204 to express untagged zacrp3 polypeptides. The zCZR204 expression vector is as described above, the only difference is that this expression plasmid has the β-glucanase leader inserted where the αFpp leader usually is. The zacrp3 sequence inserted into these vectors begins at residue 23 (Gln) of the zacrp3 amino acid sequence. The nucleotide sequence of zacrp3 is shown in SEQ ID NO:13 and the polypeptide sequence of zacrp3 is shown in SEQ ID NO:14.

For each construct specific recombination primers were designed. For the αFppD-→Y::zacrp3 construct, these primers are ZG37,475 (SEQ ID NO:15) and ZG37,474 (SEQ ID NO:16). For the β-glucanase::zacrp3 construct, the β-glucanase leader was amplified using primers ZG39,207 (SEQ ID NO:17) and ZG39,209 (SEQ ID NO:18), while zacrp3 was amplified using primers ZG39,208 (SEQ ID NO:19) and ZG37,474 (SEQ ID NO:16). The resulting PCR fragments were homologously recombined into the yeast expression vectors described above. For the αFppD →Y::zacrp3 construct, the N-terminal primer (ZG37,475) (SEQ ID NO:15) spans 39 base pairs of the alpha factor prepro (αFpp) coding sequence on one end, followed by 26 base pairs of the amino-terminus coding sequence of mature zacrp3 sequence on the other. The C-terminal primer (ZG37,474) (SEQ ID NO:16) spans about 28 base pairs of carboxy terminus coding sequence of zacrp3 on one end with 40 base pairs of AUG1 terminator sequence.

For the β-glucanase::zacrp3 construct, the N-terminal β-glucanase primer (ZG39,207) (SEQ ID NO:17) spans 40 base pairs of AUGIp sequence, followed by 27 base pairs of β-glucanase leader sequence. The C-terminal primer (ZG39,209) (SEQ ID NO:18) that amplifies β-glucanase contains 30 base pairs of carboxy terminus coding sequence of β-glucanase followed by 33 base pairs of the amino-terminus coding sequence of the Glu—Glu tag. The N-terminal zacrp3 primer (ZG39,208) (SEQ ID NO:19) spans 39 base pairs of β-glucanase sequence, followed by 26 base pairs of the mature zacrp3 sequence. The C-terminal primer (ZG37,474) (SEQ ID NO:16) that amplifies zacrp3 spans about 28 base pairs of carboxy terminus coding sequence of zacrp3 on one end with 40 base pairs of AUG1 terminator sequence.

Construction of the Untagged zacrp3 Plasmid Utilizing the αFpp Leader

An untagged zacrp3 plasmid was made by homologously recombining 100 ng of the SmaI digested pVRM51 acceptor vector and 1 µg of PCR amplified zacrp3 cDNA donor fragment, in *S. cerevisiae* SF838-9Dα.

The zacrp3 PCR fragment was synthesized by a PCR reaction. To a final reaction volume of 100 µl was added 100 pmol each of primers, ZG37,474 (SEQ ID NO:16) and ZG37,475 (SEQ ID NO:15), 10 µl of 10× PCR buffer (Boehringer Mannheim), 1 µl Pwo Polymerase (Boehringer Mannheim), 10 µl of 0.25 mM nucleotide triphosphate mix (Perkin Elmer) and dH$_2$O. The PCR reaction was run 1 cycle at 2 minutes at 94° C., followed by 25 cycles of 30 seconds at 94° C., 1 minute at 50° C. and 1 minute at 72° C., followed by a 7 minute extension at 72° C., and concluded with an overnight hold at 4° C. The resulting 754 bp double stranded, zacrp3 fragment is disclosed in SEQ ID NO:20.

Construction of the Untagged zacrp3 Plasmid Utilizing the β-glucanase Leader An untagged zacrp3 plasmid was made by homologously recombining 100 ng of the SmaI digested pCZR204 acceptor vector and 1 µg each of PCR amplified β-glucanase leader donor fragment and 1 µg zacrp3 cDNA donor fragment, in *S. cerevisiae* SF838-9Dα. The zacrp3 PCR fragments were synthesized by first amplifying the two fragments containing the β-glucanase leader and zacrp3, respectively, in separate reactions.

The β-glucanase leader was amplified in a PCR reaction as follows: to a final reaction volume of 100 µl was added 100 µmol each of primers, ZG39,207 (SEQ ID NO:17) and ZG39,209 (SEQ ID NO:18), 10 µl of 10×PCR buffer (Boehringer Mannheim), 1 µl Pwo Polymerase (Boehringer Mannheim), 10 µl of 0.25 mM nucleotide triphosphate mix (Perkin Elmer) and dH$_2$O. The PCR reaction was run 1 cycle at 2 minutes at 94° C., followed by 25 cycles of 30 seconds at 94° C., 1 minute at 50° C. and 30 seconds at 72° C., followed by a 7 minute extension at 72° C., and concluded with an overnight hold at 4° C. The resulting 157 bp double stranded, β-glucanase leader fragment is disclosed in SEQ ID NO:21.

Zacrp3 was amplified in an additional PCR reaction as follows: to a final reaction volume of 100 µl was added 100 pmol each of primers, ZG39,208 (SEQ ID NO:19) and ZG37,474 (SEQ ID NO:16), 10 µl of 10×PCR buffer (Boehringer Mannheim), 1 µl Pwo Polymerase (Boehringer Mannheim), 10 µl of 0.25 mM nucleotide triphosphate mix (Perkin Elmer) and dH$_2$O. The PCR reaction was run 1 cycle at 2 minutes at 94° C., followed by 25 cycles of 30 seconds at 94° C., 1 minute at 50° C. and 30 seconds at 72° C., followed by a 7 minute extension at 72° C., and concluded with an overnight hold at 4° C. The resulting 754 bp fragment is double stranded, and the zacrp3 PCR fragment is disclosed in SEQ ID NO:22.

One hundred microliters of competent yeast cells (*S. cerevisiae* strain SF838-9Dα) was independently combined with the various DNA mixtures from above and transferred to a 0.2 cm electroporation cuvette. The yeast/DNA mixtures were electropulsed at 0.75 kV (5 kV/cm), infinite Ω, 25 µF.

The yeast/DNA mixtures were then added to 1 ml of 1.2 M sorbitol and incubated at 30° C. for 1 hour. The yeast was then plated in two 500 µl aliquots onto two URA DS plates and incubated at 30° C.

After about 48 hours the Ura+ yeast transformants from a single plate were resuspended in 1 ml H$_2$O and spun briefly to pellet the yeast cells. The cell pellet was resuspended in 300 µl of Qiagen P1 lysis buffer and transferred to a fresh tube that contained 100–200 µl acid-washed glass beads (Sigma). Samples were vortexed for 1 minute intervals two or three times to lyse cells. Samples were allowed to settle, and 250 µl lysate was transferred to a fresh tube and the remainder of the Qiagen Spin Miniprep Kit was carried out following manufacterer's instructions.

Transformation of electrocompetent *E. coli* DH10B cells (Invitrogen) was done with 2 µl yeast DNA prep and 40 µl of DH10B cells. The cells were electropulsed in 0.1 cm cuvettes at 2.0 kV, 25 µF and 100 Ω. Following electroporation, 250 µl SOC (2% Bacto Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) was plated in one aliquot on an LB AMP plate (LB broth (Lennox), 1.8% Bacto Agar (Difco), 100 mg/L Ampicillin). Plates were incubated at 37° C. overnight.

Individual clones harboring the correct expression construct for untagged zacrp3 were identified by restriction digest to verify the presence of the zacrp3 insert and to confirm that the various DNA sequences had been joined correctly to one another. The inserts of positive clones were subjected to sequence analysis. The αfpp D→Y leader:: zacrp3 plasmid was designated pSDH147 and the β-glucanase leader::zacrp3 plasmid was designated pSDH149. Larger scale plasmid DNA was isolated for both plasmids using the Qiagen Maxi kit (Qiagen) according to manufacturer's instruction and the DNA was digested with Not I to liberate the *Pichia*-zacrp3 expression cassette from the vector backbone. The Not I-restriction digested DNA fragment was then transformed into the *Pichia methanolica* expression hosts, PMAD16 and PMAD18. This was done by mixing 100 µl of prepared competent PMAD16 or PMAD18 cells with 10 µg of Not I restriction digested pSDH147 or pSDH149, in separate transformations, and transferred to a 0.2 cm electroporation cuvette. The yeast/DNA mixture was electropulsed at 0.75 kV, 25 µF, infinite Ω. To the cuvette was added 800 µl of 1.2M Sorbitol and 400 µl aliquots were plated onto two ADE DS (0.056%-Ade-Trp-Thr powder, 0.67% yeast nitrogen base without amino acids, 2% D-glucose, 0.5% 200× tryptophan, threonine solution, and 18.22% D-sorbitol) plates for selection and incubated at 30° C.

Zacrp3 Expression in *P. methanolica* Hosts PMAD16 and PMAD18—Clone Selection and Characterization One hundred clones of each strain/plasmid (for 400 clones total) were isolated. Of these, only 10 of each were screened via Western blot for high-level zacrp3 expression. All 40 clones were grown in the following manner: 25 ml cultures of each were inoculated using one colony of each strain in BMY.1 pH6.0 media (Per liter: 13.4 g Yeast Nitrogen Base without amino acids (Becton Dickinson), 10.0 g Yeast Extract (Difco), 10.0 g tryptone (Difco), 10.0 g casamino acids (Difco), 6.7 g K$_2$HPO$_4$ (EM Science), 4.2 g citric acid (EM Science), and water)+2% glucose. BMY.1 media was supplemented with 10 mis per liter of media with FXIII vitamin solution (0.05 g/L biotin, 0.8 g/L thiamine hydrochloride, 0.8 g/L pyroxidine HCL, 15.0 g/L inositol, 15.0 g/L calcium pantothenate, 0.6 g/L niacinamide, 0.1 g/L folic acid, 0.2 g/L riboflavin, 1.0 g/L choline chloride). Cultures were grown in 125 ml baffled flasks on a platform shaker set to 250 rpm at 30° C. overnight.

The following day, 1 ml of each overnight inoculum culture was diluted into 24 mls of fresh BMY.1 media supplemented with FXIII vitamins as above, +1% Methanol to induce the AUG1 promoter (no glucose was added). Cultures were grown in 125 ml baffled flasks on a platform shaker set to 250 rpm at 30° C. for 24 hours. After 24 hours of growth and induction, the cultures were harvested at 5000 rpm for 10 minutes in a Beckman centrifuge (JA-20 rotor) to pellet the cells. Three hundred µl of zacrp3 containing supernatant was mixed with 100 µl of NuPAGE 4× Sample Buffer (Invitrogen). Each 400 µl sample was split into two 200 µl samples: one set of samples was treated with 2% β-mercaptoethanol (Sigma) and represents a reduced sample, while the other set represents the non-reduced sample.

An SDS-PAGE analysis was carried out as described below. All reduced samples were heated for 10 min at 100° C., while all non-reduced samples were heated for 10 min at 65° C. Fifteen µL of each sample was applied for electrophoresis on a polyacrylamide gel. Protein separation was performed by electrophoresis in a 4–12% gradient NuPAGE polyacrylamide resolving gel (Invitrogen) under denaturing conditions (SDS-PAGE) using 1×MES running buffer (Invitrogen). The voltage of 130V was applied throughout the entire run. Subsequently, electrotransference was carried out to a 0.2 µn nitrocellulose membrane (Invitrogen) for 1 h at 400 mA (constant current). The blots were then incubated for 30 minutes with agitation at 40 rpm in a blocking solution [Western A+10% non-fat dry milk (NFDM)(Carnation)] in order to block the protein-free areas of the membrane at 25° C.

As the first antibody, an anti-zacrp3 affinity purified antibody, E1834, developed in the rabbit (in-house) was used in a dilution of 1:10,000 in Western A+2.5% NFDM. Incubation was 2 hours at 25° C. Subsequently two 5 min. washings were performed at moderate agitation with Western B, followed by one 5 minute was at moderate agitation with Western A. As the second antibody a rabbit anti-IgG developed in the goat (Amersham) was used in a dilution of 1:2000 in Western A+2.5% NFDM. Blots were incubated for 1 hour at room temperature and washed three times for 5 min with moderate agitation with Western B, followed by a brief rinse in dH$_2$O. Two mls of both Enhanced Chemiluminescent substrates (Amersham) were mixed together at a 1:1 ratio, and the blots were incubated in this solution for 5 seconds prior to development. The exposed blots were then developed using timed exposure to X-ray film (Kodak) and the film was subsequently developed to visualize data.

The electrophoretic analysis on the polyacrylamide gel of the culture medium from *P. methanolica* clones representing pSDH149 (β-glucanase leader) and pSDH147 (*S. cerevisiae* alpha factor pre-pro sequence) showed that in the culture medium from both host strains a band of approximately 28 kDa (under reduced conditions) appears corresponding to zacrp3, while in the non-induced cell culture medium, there was no band. Roughly ninety percent of the recombinant clones that were analyzed for the integrated heterologous gene expression produced and secreted recombinant zacrp3. The resulting zacrp3 plasmid-containing yeast strains show the endogenous *P. methanolica* β-glucanase leader construct pSDH149 secretes equivalent levels of zacrp3 compared to the heterologous *S. cerevisiae* αFpp leader pSDH147 in the PMAD16 host strain background. Interestingly, plasmid-containing yeast strains show the endogenous *P. methanolica* β-glucanase leader construct pSDH149 secretes approximately 2–3 fold higher levels of zacrp3 compared to the heterologous *S. cerevisiae* αFpp leader pSDH147 in the PMAD18 host strain background. One isolet of each αFpp:: zacrp3 strain was picked for subsequent use; the resulting clones were designated PMAD16::pSDH147.4.2, PMAD18::pSDH147.4.8, respectively. Two isolets of each β-glucanase::zacrp3 strain was picked for subsequent use; the resulting clones were designated PMAD16:: pSDH149.4.4, PMAD16::pSDH149.4.9, PMAD18:: pSDH149.4.5, and PMAD18::pSDH149.4.8, respectively.

Example 3

Construction and Characterization of Zsig37 Untagged Yeast Expression Vectors

Utilizing a Heterologous *S. cerevisiae* Leader and an Endogenous *P. methanolica* Leader Expression of zsig37 in *Pichia methanolica* utilizes the expression system as described in Raymond, U.S. Pat. No. 5,888,768; Raymond, U.S. Pat. No. 5,955,349; and Raymond, U.S. Pat. No. 6,001,597. An expression plasmid containing all or part of a polynucleotide encoding zsig37 is constructed via homologous recombination (Raymond et al., U.S. Pat. No. 5,854,039). Zsig37 was recombined into the vector pCZR204. Oligos used to amplify zsig37 introduced a single amino acid mutation (D83→Y83) within the alpha factor prepro (αFpp) sequence to enhance Kex2p cleavage. This mutation was then introduced into the vector pCZR204 when recombination occurred. The pCZR204 vector contains the AUG1 promoter, followed by the αfpp leader sequence and an amino-terminal peptide tag (Glu—Glu), followed by a blunt-ended Sma I restriction site, a carboxy-terminal peptide tag (Glu—Glu), a translational STOP codon, followed by the AUG1 terminator, the ADE2 selectable marker, and finally the AUG1 3' untranslated region. Also included in this vector are the URA3 and CEN-ARS sequences required for selection and replication in *S. cerevisiae*, and the AmpR and colE1 ori sequences required for selection and replication in *E. coli*. A second expression vector was built from zCZR204 to express untagged zsig37 polypeptides. The zCZR204 expression vector is as described above, the only difference is that this expression plasmid has the β-glucanase leader inserted where the αFpp leader usually is. The zsig37 sequence inserted into these vectors begins at residue 86 (Arg) of the zsig37 amino acid sequence. The full-length nucleotide sequence of zsig37 is shown in SEQ ID NO:27 and the full-length polypeptide sequence of zsig37 is shown in SEQ ID NO:28 (See U.S. Pat. Nos. 6,265,544, 6,566,499, 6,518,403, 6,448,221, and 6,544,946).

For each construct specific recombination primers were designed. For the αFppD83→Y83::zsig37 construct, these primers are ZG42,210 (SEQ ID NO:29) and ZG42,206 (SEQ ID NO:30). For the β-glucanase::zsig37 construct, the β-glucanase leader was amplified using primers ZG42,209 (SEQ ID NO:31) and ZG42,211 (SEQ ID NO:32), while zsig37 was amplified using primers ZG42,273 (SEQ ID NO:33) and ZG42,206 (SEQ ID NO:30). The resulting PCR fragments were homologously recombined into the yeast expression vector described above. For the αFppD83→Y83::zsig37 construct, the N-terminal primer (ZG42,210) (SEQ ID NO:29) spans 39 base pairs of the alpha factor prepro (αFpp) coding sequence on one end, and introduces the D83→Y83 mutation in the αFpp sequence, followed by 25 base pairs of the amino-terminus coding sequence of mature zsig37 sequence on the other. The C-terminal primer (ZG42,206) (SEQ ID NO:30) spans about 21 base pairs of carboxy terminus coding sequence of zsig37 on one end with 40 base pairs of AUG1 terminator sequence.

For the β-glucanase::zsig37 construct, the N-terminal β-glucanase primer (ZG42,209) (SEQ ID NO:31) spans 40 base pairs of AUG1p sequence, followed by 27 base pairs of β-glucanase leader sequence. The C-terminal primer (ZG42, 211) (SEQ ID NO:32) that amplifies β-glucanase contains 39 base pairs of carboxy terminus coding sequence of β-glucanase followed by 25 base pairs of the amino-terminus coding sequence of the mature zsig37 sequence. The N-terminal zsig37 primer (ZG42,273) (SEQ ID NO:33) spans 39 base pairs of β-glucanase sequence, followed by 25 base pairs of the mature zsig37 sequence. The C-terminal primer (ZG42,206) (SEQ ID NO:30) that amplifies zsig37 spans about 21 base pairs of carboxy terminus coding sequence of zsig37 on one end with 40 base pairs of AUG1 terminator sequence.

Construction of the Untagged zsig37 Plasmid Utilizing the αFppD→Y Leader

An untagged zsig37 plasmid was made by homologously recombining 100 ng of the SmaI digested pCZR204 acceptor vector and 1 µg of PCR amplified zsig37 cDNA donor fragment, in *S. cerevisiae* SF838-9Dα.

The zsig37 PCR fragment was synthesized by a PCR reaction. To a final reaction volume of 100 µl was added 100 pmol each of primers, ZG42,210 (SEQ ID NO:29) and ZG42,206 (SEQ ID NO:30), 10 µl of 10×PCR buffer (Boehringer Mannheim), 1 µl Pwo Polymerase (Boehringer Mannheim), 10 µl of 0.25 mM nucleotide triphosphate mix (Perkin Elmer) and dH$_2$O. The PCR reaction was run 1 cycle at 2 minutes at 94° C., followed by 30 cycles of 30 seconds at 94° C., 1 minute at 50° C. and 1 minute at 72° C., followed by a 7 minute extension at 72° C., and concluded with an overnight hold at 4° C. The resulting 846 bp double stranded, zsig37 fragment is disclosed in SEQ ID NO:34. The αFpp:zsig37 full-length nucleotide (pSDH156) is shown in SEQ ID NO:35, with its corresponding encoded protein shown in SEQ ID NO:36.

Construction of the Untagged zsig37 Plasmid Utilizing the α-glucanase Leader

An untagged zsig37 plasmid was made by homologously recombining 100 ng of the SmaI digested pCZR204 acceptor vector and 1 µg each of PCR amplified β-glucanase leader donor fragment and 1 µg zsig37 cDNA donor fragment, in *S. cerevisiae* SF838-9Dα. The zsig37 PCR fragments were synthesized by first amplifying the two fragments containing the β-glucanase leader and zsig37, respectively, in separate reactions.

The β-glucanase leader was amplified in a PCR reaction as follows: to a final reaction volume of 100 µl was added 100 pmol each of primers, ZG42,209 (SEQ ID NO:31) and ZG42,211 (SEQ ID NO:32), 10 µl of 10×PCR buffer (Boehringer Mannheim), 1 µl Pwo Polymerase (Boehringer Mannheim), 10 µl of 0.25 mM nucleotide triphosphate mix (Perkin Elmer) and dH$_2$O. The PCR reaction was run 1 cycle at 2 minutes at 94° C., followed by 30 cycles of 30 seconds at 94° C., 1 minute at 50° C. and 1 minute at 72° C., followed by a 7 minute extension at 72° C., and concluded with an overnight hold at 4° C. The resulting 148 bp double stranded, β-glucanase leader fragment is disclosed in SEQ ID NO:37.

Zsig37 was amplified in an additional PCR reaction as follows: to a final reaction volume of 100 µl was added 100 pmol each of primers, ZG42,273 (SEQ ID NO:33) and ZG42,206 (SEQ ID NO:30), 10 µl of 10×PCR buffer (Boehringer Mannheim), 1 µl Pwo Polymerase (Boehringer Mannheim), 10 µl of 0.25 mM nucleotide triphosphate mix (Perkin Elmer) and dH$_2$O. The PCR reaction was run 1 cycle at 2 minutes at 94° C., followed by 30 cycles of 30 seconds at 94° C., 1 minute at 50° C. and 1 minute at 72° C., followed by a 7 minute extension at 72° C., and concluded with an overnight hold at 4° C. The resulting 846 bp fragment is double stranded, and the zsig37 PCR fragment is disclosed in SEQ ID NO:38.

One hundred microliters of competent yeast cells (*S. cerevisiae* strain SF838-9Dα) was independently combined with the various DNA mixtures from above and transferred to a 0.2 cm electroporation cuvette. The yeast/DNA mixtures were electropulsed at 0.75 kV (5 kV/cm), infinite Ω, 25 µF. The yeast/DNA mixtures were then added to 1 ml of 1.2 M sorbitol and incubated at 30° C. for 1 hour. The yeast was then plated in two 500 µl aliquots onto two URA DS plates and incubated at 30° C.

After about 48 hours the Ura+ yeast transformants from a single plate were resuspended in 1 ml H$_2$O and spun briefly to pellet the yeast cells. The cell pellet was resuspended in 300 µl of Qiagen P1 lysis buffer and transferred to a fresh tube that contained 100–200 µl acid-washed glass beads (Sigma). Samples were vortexed for 1 minute intervals two or three times to lyse cells. Samples were allowed to settle, and 250 µl lysate was transferred to a fresh tube and the remainder of the Qiagen Spin Miniprep Kit was carried out following manufacterer's instructions.

Transformation of electrocompetent *E. coli* DH10B cells (Invitrogen) was done with 2 µl yeast DNA prep and 40 ul of DH10B cells. The cells were electropulsed in 0.1 cm cuvettes at 2.0 kV, 25 µF and 100 Ω. Following electroporation, 250 µl SOC (2% Bacto Tryptone (Difco, Detroit, Mich.), 0.5% yeast extract (Difco), 10 mM NaCl (J. T. Baker), 2.5 mM KCl (Mallinkrodt), 10 mM MgCl$_2$ (Mallinkrodt), 10 mM MgSO$_4$ (J. T. Baker), 20 mM glucose (Difco) and water) was plated in one aliquot on an LB AMP plate (LB broth (Lennox), 1.8% Bacto Agar (Difco), 100 mg/L Ampicillin (Sigma)). Plates were incubated at 37° C. overnight.

Individual clones harboring the correct expression construct for untagged zsig37 were identified by restriction digest to verify the presence of the zsig37 insert and to confirm that the various DNA sequences had been joined correctly to one another. The inserts of positive clones were subjected to sequence analysis. The αFpp D83→Y83 leader::zsig37 plasmid was designated pSDH156 and the β-glucanase leader::zsig37 plasmid was designated pSDH160. Larger scale plasmid DNA was isolated for both plasmids using the Qiagen Maxi kit (Qiagen) according to manufacturer's instruction and the DNA was digested with Not I to liberate the *Pichia*-zsig37 expression cassette from the vector backbone. The Not I-restriction digested DNA fragment was then transformed into the *Pichia methanolica* expression hosts, PMAD16 and PMAD18. This was done by mixing 100 µl of prepared competent PMAD16 or PMAD18 cells with 1.0 µg and 2.5 µg of Not I restriction digested pSDH156 or pSDH160, in separate transformations, and transferred to a 0.2 cm electroporation cuvette. The yeast/DNA mixture was electropulsed at 0.75 kV, 25 µF, infinite Ω.

To the cuvette was added 800 µl of 1.2M Sorbitol. Transformants were outgrown in test tubes at 30° C. for 2 hours prior to plating on selection plates. Four hundred µl aliquots were plated onto two ADE DS (0.056%-Ade-Trp-Thr powder (TCI America, Alfa Aesar, and Calbiochem), 0.67% yeast nitrogen base without amino acids (Becton Dickinson), 2% D-glucose (Difco), 0.5% 200× tryptophan, threonine solution (ICN and Alfa Aesar), and 18.22% D-sorbitol) plates for selection and incubated at 30° C. The β-glucanase::zsig37 full-length nucleotide sequence (pSDH160) is shown in SEQ ID NO:39, with its corresponding encoded protein shown in SEQ ID NO:40.

Zsig37 Expression in *P. methanolica* Hosts PMAD16 and PMAD18—Clone Selection and Characterization Two hundred fifty clones of PMAD16::pSDH156 and 300 clones of PMAD18::pSDH156 were isolated. In addition, 55 clones of PMAD16::pSDH160 and 68 clones of PMAD18::pSDH160 were isolated. All clones were screened via colony blot analysis for high-level zsig37 expression. Clones were screened by colony blot as follows: each transformant was patched to two fresh 1% Methanol plates (Per liter: 6.8 g Yeast Nitrogen Base without amino acids (Becton Dickinson), 0.6 g-ade-trp-thr powder (TCI America, Alfa Aesar, Calbiochem), 18.0 g Bacto agar (Difco), 5 mls 200× Tryptophan/threonine solution (Alfa Aesar and ICN), 10 mls Methanol (J. T. Baker), 2 mls saturated biotin (ICN) and water). Each plate was overlayed with a nitrocellulose filter (Schleicher & Schuell) and incubated at 30° C. for 3 days. Nitrocellulose filters were then removed. One set of filters was denatured and reduced under the following conditions: filters were placed in a hybridization tube and 25 mls of 25 mM Tris (Millipore), 25 mM Glycine (J. T. Baker), 5 mM β-ME (Sigma) pH9.0 was added to each tube. Filters were incubated at 65° C. for 10 minutes. Post-denaturation/reduction, filters were removed and placed directly in Western block solution (50 mM Tris (Millipore) pH7.4, 5 mM EDTA (J. T. Baker) pH8.0, 0.05% Igepal CA-630 (Sigma), 150 mM NaCl (J. T. Baker), 2.5% Gelatin (Mallinkrodt), water and 10% nonfat dry milk (NFDM)(Carnation)). The other identical set of filters represents a non-denatured, non-reduced set of filters. These filters were removed from the plates and placed directly into Western block solution. All filters were incubated in block solution for 30 minutes at 25° C.

Filters were then incubated in Western A (50 mM Tris (Millipore) pH7.4, 5 mM EDTA (J. T. Baker) pH8.0, 0.05% Igepal CA-630 (Sigma), 150 mM NaCl (J. T. Baker), 2.5% Gelatin (Mallinkrodt), water)+2.5% NFDM (Carnation) containing 0.2 µg/ml zsig37 primary antibody E1489 for 1–2 hours at 25° C. Blots were then washed 3 times for 7 minutes each at 25° C. in Western B (1M NaCl (J. T. Baker), 50 mM Tris (Millipore) pH7.4, 5 mM EDTA (J. T. Baker), 0.05% Igepal (Sigma), 0.25% gelatin (Mallinkrodt), and water) followed by one wash in Western A for 7 minutes at 25° C. Filters were then incubated in Western A+2.5% NFDM containing a 1:5000 dilution of donkey anti rabbit secondary antibody (Life Technologies) for 1 hour at 25° C. Blots were then washed 4 times for 7 minutes each at 25° C. in Western B (1M NaCl (J. T. Baker), 50 mM Tris (Millipore) pH7.4, 5 mM EDTA (J. T. Baker), 0.05% Igepal (Sigma), 0.25% gelatin (Mallinkrodt), and water) at 25° C. All blots were then briefly rinsed with deionized water before being developed with Lumi-Light Plus ECL substrate (Roche). Two mls of both Lumi-Light substrates were mixed together at a 1:1 ratio, and the blots were incubated in this solution for 5 seconds prior to development. The exposed blots were then developed using timed exposure to X-ray film (Kodak) and the film was subsequently developed to visualize data.

Ten clones of PMAD16::pSDH156, 12 clones of PMAD18::pSDH156, 6 clones of PMAD16::pSDH160 and 6 clones of PMAD18::pSDH160 were picked for follow-up western analysis. All clones were grown in the following manner: 5 ml cultures of each were inoculated using one colony of each strain in YEPD media (Per liter: 20.0 g D-Glucose (J. T. Baker), 20.0 g Bacto Peptone (Difco), 10.0 g Yeast Extract (Difco), 0.04 g adenine (Alfa Aesar), 0.06 g L-Leucine (TCI America) and water). Cultures were grown in test tubes and placed on a roller drum at 30° C. overnight. The following day, 0.5 ml of each overnight inoculum culture was diluted into 24.5 mls of BMY.1 media (Per liter: 13.4 g Yeast Nitrogen Base without amino acids (Becton Dickinson), 10.0 g Yeast Extract (Difco), 10.0 g tryptone (Difco), 10.0 g casamino acids (Difco), 6.7 g $K_2HPO_4$ (EM Science), 4.2 g citric acid (EM Science), and water) supplemented with 10 mls per liter of media with FXIII vitamin solution (0.05 g/L biotin, 0.8 g/L thiamine hydrochloride, 0.8 g/L pyroxidine HCL, 15.0 g/L inositol, 15.0 g/L calcium pantothenate, 0.6 g/L niacinamide, 0.1 g/L folic acid, 0.2 g/L riboflavin, 1.0 g/L choline chloride) and 10 mls per liter of Methanol (J. T. Baker) for a 1% Methanol final concentration. Cultures were grown in 125 ml baffled flasks on a platform shaker set to 250 rpm at 30° C. for 48 hours. After 24 hours, a sample was taken for western analysis, and a 1% Methanol dose was added to each culture.

After 48 hours of growth and induction, the cultures were harvested at 10,000 rpm for 10 minutes in a Beckman centrifuge (JA-20 rotor) to pellet the cells. Two hundred fifty μl of zsig37 containing supernatant was mixed with 250 μl of 2× Laemmli Sample Buffer (125 mM Tris (Millipore), 20% glycerol (EM Science), 4% SDS (ICN), 0.01% Bromophenol blue (EM Science) and water). Each 500 μl sample was split into two 250 μl samples: one set of samples was treated with 2% β-mercaptoethanol (Sigma) and represents a reduced sample, while the other set represents the non-reduced sample.

An SDS-PAGE analysis was carried out as described below. All reduced samples were heated for 10 min at 65° C., while all non-reduced samples were not heated. Fifteen μL of each sample was applied for electrophoresis on a polyacrylamide gel. Protein separation was performed by electrophoresis in a 4–12% gradient Tris-Gly polyacrylamide resolving gel (Invitrogen) under denaturing conditions (SDS-PAGE) using 1× Glycine running buffer (Invitrogen). The voltage of 80V was applied for the first 30 minutes, then the voltage was raised to 130V for the duration of the run. Subsequently, electrotransference was carried out to a 0.2 μm nitrocellulose membrane (Invitrogen) for 2 h at 200 mA (constant current). The blots were then developed as above.

The electrophoretic analysis on the polyacrylamide gel of the culture medium from *P. methanolica* clones representing pSDH156 (*S. cerevisiae* alpha factor D→Y pre-pro sequence) and pSDH160 (β-glucanase leader) showed that in the culture medium from both host strains a milieu appears corresponding to various zsig37 forms, while in the non-induced cell culture medium, there was no band. Roughly ninety percent of the recombinant clones that were analyzed for the integrated heterologous gene expression produced and secreted recombinant zsig37. The resulting zsig37 plasmid-containing yeast strains show the heterologous *S. cerevisiae* αFpp construct pSDH156 secretes equivalent levels of zsig37 compared to the endogenous *P. methanolica* β-glucanase leader pSDH160 in the PMAD16 host strain background. Interestingly, plasmid-containing yeast strains show the endogenous *P. methanolica* β-glucanase leader construct pSDH160 secretes approximately 2–3 fold higher levels of zsig37 in PMAD16 compared to the PMAD18 host strain background. Every isolet of each αFpp::zsig37 strain was picked for subsequent use; the resulting clones were designated PMAD16::pSDH156 isolets #40, 56, 58, 84, 92, 149, 167, 169, 230, 231, and PMAD18::pSDH156 isolets #23, 29, 35, 144, 149, 161, 191, 202, 206, 217, 224, 269, respectively. In addition, every isolet of each β-glucanase::zsig37 strain was picked for subsequent use; the resulting clones were designated PMAD16::pSDH160 isolets #1, 2, 26, 30, 44, and PMAD18::pSDH160 isolets #1, 10, 21, 43, 48, 62, respectively.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An isolated DNA molecule comprising a nucleotide sequence of SEQ ID NO:1 or complement thereof.

2. An isolated DNA molecule capable of hybridizing to SEQ ID NO:1, or a complement thereof, under hybridization conditions of 0.015 M NaCl/0.0015 M sodium citrate (SSC) and about 0.1% sodium dodecyl sulfate (SDS) at about 50° C. to about 65° C., wherein the DNA molecule encodes a polypeptide that is a secretory signal sequence of *Pichia methanolica*.

3. The isolated DNA molecule of claim 2 wherein the encoded polypeptide has at least 20 contiguous amino acids of SEQ ID NO:2.

4. The isolated DNA molecule of claim 2 wherein the encoded polypeptide is SEQ ID NO:2.

5. An isolated DNA molecule encoding a polypeptide wherein the encoded polypeptide comprises an amino acid sequence having at least 95 percent sequence identity to SEQ ID NO:2, wherein the encoded polypeptide is a secretory signal sequence of *Pichia methanolica*.

6. The isolated DNA molecule of claim 5 wherein the encoded polypeptide comprises SEQ ID NO:2.

7. The isolated DNA molecule of claim 5 wherein the encoded polypeptide is SEQ ID NO:2.

8. A DNA construct comprising the following operably linked elements:
a first DNA segment comprising a transcription promoter of *Pichia methanolica*;
a second DNA segment comprising a nucleotide sequence encoding a polypeptide of SEQ ID NO:2;
a third DNA segment encoding a heterologous protein of interest; and
a fourth DNA segment comprising a transcription terminator of *Pichia methanolica*.

9. The DNA construct of claim 8 wherein the first DNA segment is a *Pichia methanolica* transcription promoter selected from the group consisting of glyceraldehyde-3-phosphate dehydrogenase 1 (GAP1), glyceraldehyde-3-phosphate dehydrogenase 2 (GAP2), alcohol utilization gene 1 (AUG1), and alcohol utilization gene 2 (AUG2).

10. The DNA construct of claim 8 wherein the second DNA segment comprises SEQ ID NO:1.

11. The DNA construct of claim 8 wherein the second DNA segment is SEQ ID NO:1.

12. The DNA construct of claim 8 wherein the fourth DNA segment comprises a *Pichia methanolica* transcription terminator selected from the group of genes consisting of GAP1, GAP2, AUG1, and AUG2.

13. The DNA construct of claim 8 further comprising a selectable marker.

14. The DNA construct of claim 13 wherein the selectable marker is an ADE2 gene.

15. The DNA construct of claim 8 further comprising a *Pichia methanolica* origin of replication.

16. The DNA construct of claim 8 further comprising a fifth operably linked DNA segment wherein the fifth DNA segment comprises an affinity tag, a therapeutic agent or a detectable label.

17. The DNA construct of claim 8 further comprising a fifth operably linked DNA segment wherein the fifth DNA segment comprises an immunoglobulin moiety comprising at least one constant region.

18. The DNA construct of claim 17 wherein the fifth DNA segment is a human immunoglobulin Fc fragment.

19. A *Pichia methanolica* cell containing the DNA construct of claim 8.

20. The *Pichia methanolica* cell of claim 19 wherein the DNA construct is genomically integrated.

21. The *Pichia methanolica* cell of claim 20 wherein the DNA construct is genomically integrated in multiple copies.

22. The *Pichia methanolica* cell of claim 19 wherein the cell is functionally deficient in vacuolar proteinase A.

23. The *Pichia methanolica* cell of claim 19 wherein the cell is functionally deficient in vacuolar proteinase B.

24. The *Pichia methanolica* cell of claim 19 wherein the cell is functionally deficient in vacuolar protease A and vacuolar protease B.

25. The *Pichia methanolica* cell of claim 19 wherein the cell comprises a functionally deficient AUG1 gene.

26. The *Pichia methanolica* cell of claim 19 wherein the cell comprises a functionally deficient AUG2 gene.

27. The *Pichia methanolica* cell of claim 19 wherein the cell comprises functionally deficient AUG1 and AUG2 genes.

28. A method of producing a protein of interest comprising:
culturing the cell of claim 19 wherein the third DNA segment is expressed and the protein of interest is produced; and
recovering the protein of interest.

* * * * *

SEQUENCE LISTING

```
<160> NUMBER OF SEQ ID NOS: 40

<210> SEQ ID NO 1
<211> LENGTH: 84
<212> TYPE: DNA
<213> ORGANISM: Pichia methanolica
<220> FEATURE:
<221> NAME/KEY: CDS
<222> LOCATION: (1)...(84)

<400> SEQUENCE: 1 atg aag ttc tcg cta agt aca ttg aca gtt atc acc acc tta cta tca    48
Met Lys Phe Ser Leu Ser Thr Leu Thr Val Ile Thr Thr Leu Leu Ser
 1               5                  10                  15
```

```
ttg gtc tca gct gca cca ctc act ttg aaa aag aga                         84
Leu Val Ser Ala Ala Pro Leu Thr Leu Lys Lys Arg
            20                  25

<210> SEQ ID NO 2
<211> LENGTH: 28
<212> TYPE: PRT
<213> ORGANISM: Pichia methanolica

<400> SEQUENCE: 2

Met Lys Phe Ser Leu Ser Thr Leu Thr Val Ile Thr Thr Leu Leu Ser
1               5                   10                  15

Leu Val Ser Ala Ala Pro Leu Thr Leu Lys Lys Arg
            20                  25

<210> SEQ ID NO 3
<211> LENGTH: 84
<212> TYPE: DNA
<213> ORGANISM: Artificial Sequence
<220> FEATURE:
<223> OTHER INFORMATION: Degenerate polynucleotide encoding SEQ ID NO:2
<220> FEATURE:
<221> NAME/KEY: variation
<222> LOCATION: (1)...(84)
<223> OTHER INFORMATION: n = A, T, G or C

<400> SEQUENCE: 3
atgaarttyw snytnwsnac nytnacngtn athacnacny tnytnwsnyt ngtnwsngcn       60
gcnccnytna cnytnaaraa rmgn                                              84

<210> SEQ ID NO 4
<211> LENGTH: 3077
<212> TYPE: DNA
<213> ORGANISM: Pichia methanolica

<400> SEQUENCE: 4
cagctgctct gctccttgat tcgtaattaa tgttatcctt ttactttgaa ctcttgtcgg       60
tccccaacag ggattccaat cggtgctcag cgggatttcc catgaggttt ttgacaactt     120
tattgatgct gcaaaaactt ttttagccgg gtttaagtaa ctgggcaata tttccaaagg     180
ctgtgggcgt tccacactcc ttgcttttca taatctctgt gtattgtttt attcgcattt     240
tgattctctt attaccagtt atgtagaaag atcggcaaac aaaatatcaa cttttatctt     300
gaacgctgac ccacggtttc aaataactat cagaactcta tagctatagg ggaagtttac     360
tgcttgctta aagcggctaa aaagtgtttg caaattaaa aaagctgtga caagtaggaa      420
ctcctgtaaa gggccgattc gacttcgaaa gagcctaaaa acagtgacta ttggtgacgg     480
aaaattgcta aaggagtact agggctgtag taataaataa tggaacagtg gtacaacaat     540
aaaagaatga cgctgtatgt cgtagcctgc acgagtagct cagtggtaga gcagcagatt     600
gcaaatctgt tggtcaccgg ttcgatccgg tctcgggctt cctttttgc ttttttcgata    660 tttgcgggta ggaagcaagg tctagttttc gtcgtttcgg atggtttacg aaagtatcag     720
ccatgagtgt ttccctctgg ctacctaata tatttattga tcggtctctc atgtgaatgt     780
ttctttccaa gttcggcttt cagctcgtaa atgtgcaaga aatatttgac tccagcgacc     840
tttcagagtc aaattaattt tcgctaacaa tttgtgtttt tctggagaaa cctaaagatt     900
taactgataa gtcgaatcaa catctttaaa tcctttagtt aagatctctg cagcggccag     960
tattaaccaa tagcatattc acaggcatca catcggaaca ttcagaatgg actcgcaaac    1020
tgtcgggatt taggtggtg ccaacttggt cgtatgatc gttgaagctg cacacagatt      1080
```

-continued

```
gaatatcaaa actgtgattc tcgaaaatgg agaccaggct ccagcaaagc aaatcaacgc    1140
tttagatgac catattgacg gctcattcaa tgatccaaaa gcaattgccg aattggctgc    1200
caagtgtgat gttttaaccg ttgagattga acatgttgac actgatgcgt tggttgaagt    1260
tcaaaaggca actggcatca aaatcttccc atcaccagaa actatttcat tgatcaaaga    1320
taaatacttg caaaagagc atttgattaa gaatggcatt gctgttgccg aatcttgtag    1380
tgttgaaagt agcgcagcat ctttagaaga agttggtgcc aaatacggct tcccatacat    1440
gctaaaatct agaacaatgg cctatgacgg aagaggtaat tttgttgtca agacaagtc    1500 atatatacct gaagctttga agttttaga tgacaggccg ttatacgccg agaaatgggc    1560
tccattttca aaggagttag ctgttatggt tgtgagatca atcgatggcc aagtttattc    1620
ctacccaact gttgaaacca tccaccaaaa caacatctgt cacactgtct tgctccagc    1680 tagagttaac gatactgtcc aaaagaaggc ccaaattttg gctgacaacg ctgtcaaatc    1740
tttcccaggt gctggtatct tggtgttga atgttttta ttacaaaatg gtgacttatt    1800
agtcaacgaa attgccccaa gacctcacaa ttctggtcac tataccatcg acgcttgtgt    1860
cacctcgcaa tttgaagctc atgttagggc cattactggt ctacccatgc cgaagaactt    1920
cacttgtttg tcgactccat ctacccaagc tattatgttg aacgttttag gtggcgatga    1980
gcaaaacggt gagttcaaga tgtgtaaaag agcactagaa actcctcatg cttctgttta    2040
cttatacggt aagactacaa gaccaggcag aaaaatgggt cacattaata tagtttctca    2100
atcaatgact gactgtgagc gtagattaca ttacatagaa ggtacgacta acagcatccc    2160
tctcgaagaa cagtacacta cagattccat tccgggcact tcaagcaagc cattagtcgg    2220
tgtcatcatg ggttccgatt cggacctacc agtcatgtct ctaggttgta atatattgaa    2280
gcaatttaac gttccatttg aagtcactat cgtttccgct catagaaccc cacaaagaat    2340
ggccaagtat gccattgatg ctccaaagag agggttgaag tgcatcattg ctggtgctgg    2400
tggtgccgct catttaccgg gaatggttgc ggcgatgacg ccgctgcctg ttattggtgt    2460
ccctgttaaa ggctctactt tggatggtgt tgattcacta cactccatcg ttcaaatgcc    2520
aagaggtatt cctgttgcta ctgtggctat taacaatgct actaacgctg ccttgctagc    2580
tatcacaatc ttaggtgccg gcgatccaaa tacttgtctg caatggaagt ttatatgaac    2640
aatatggaaa atgaagtttt gggcaaggct gaaaaattgg aaaatggtgg atatgaagaa    2700
tacttgagta catacaagaa gtagaaacctt ttatatttga tatagtactt actcaaagtc    2760
ttaattgttc taactgttaa tttctgctttt gcatttctga aaagtttaag acaagaaatc    2820
ttgaaatttc tagttgctcg taagaggaaa cttgcattca aataacatta acaataaatg    2880
acaataatat attatttcaa cactgctata tggtagtttt ataggtttgg ttaggatttg    2940
agatattgct agcgcttatc attatcctta attgttcatc gacgcaaatc gacgcatttc    3000
cacaaaaatt ttccgaacct gttttttcact tctccagatc ttggtttagt atagcttttg    3060
acacctaata cctgcag                                                   3077
```

<210> SEQ ID NO 5
<211> LENGTH: 4409
<212> TYPE: DNA
<213> ORGANISM: Pichia methanolica
<220> FEATURE:
<221> NAME/KEY: CDS
<222> LOCATION: (1733)...(2734)

<400> SEQUENCE: 5

-continued

```
cccggggat cttatttct gcaagaactt aaccgaggga catgtcaaac caagcatact      60
gtaaaagaaa tagccgatgg tttatatata tatatacttg cgttagtaga aacagtttat     120
gcatgcatgg atgcaagaac tcagatatca ggttatcaag aaacatggag aaattcctaa    180
acagaaacgg aattaatccg aaattctcgg tctcccaaag aaaatagatg cacaagctaa    240
tacagcttgc taactagctt caactttcaa aaaaaattct aagctattga atattcatca    300
agataatagt ctatataaag atgtaaagtc attattattg ggatatataa acgtcctata    360
tattgctgaa atgttaggtg tatgtactga aaacaatcag tttgagttta ccagagagag    420
acgatggatc tacagatcaa tagagagaga ataagatgag aataagatga ttaatagtga    480
gaggtagtag ccactggcgg gaggatgaaa atatcccgga taaacttaga agaaattaa     540
ttacacgtat aggtaacatt tgttattgtc gaatctcaga tcagttgatg cctggaacag    600
atcgacttat agatattatc agatcataat catgaggcga ggtgcgacta gtaccaggtg    660
atgatatatt gtttccggtt atttcaaata gttgacgtcg ttgtgtgatt gggaaggcgt    720
cggagtaaca gaaacagtaa cggtacaagc atcattatga gttgagggta tgtagggaag    780
cagttgtttg taagcatgtt tacaaatgca atgcatgtta cgattggact acaattaaat    840
ccgaatgtac ctatataacg tgttgtacgt gttgtgccgt aagtagcccg atactagatg    900
cttactacgt cactgatctg ttcggatctc agtccattca tgtgtcaaaa tagttagtag    960
ctaaggggga tacagggaag atgtttggta cgattatcgg agggatgtgt cttctgaggg   1020
gggaggagag agggcgtgta aggagtttgt ttgtttgttt gtttgttgag agaaggggg    1080
gagaagaggg ggtggtgggc tgatggcaat tgatatagag ggagagtgtg cgttaactgt   1140
ttagtgtggt ggcggtacgg ggtacactgt agaggggggac attataatgg ttatgtgtat   1200
atgctgtata tatgaataca agtagggagt gactacacat tgcaattgat aatatgtgta   1260
tgtgtgcgca tcagtatata cactcggagg ttctgaaagc catcattgta ttggacgttt   1320
gaatggtatt agatgacttg ttgtactaga ggacggagaa tgggtgagtg aagcaatag    1380
ataataatgg aaagtttgct cggtggtgga cattggcccg gagtagtgat accgtcacct   1440
taaaattgca gttaggggat gatgctccgg ggcacgacct gccaactaat ttaatagtcg   1500
tctaacgctg gaacaggtgt tgttccacaa gtagatgagt tgttggttg gctggtcaaa    1560
tgctgccttg atccatcgtt ttatatataa agactcactt ctcctcctct tgttcaattg   1620
tttcacactc aactgcttct cccttatctt ttttttttcc ctgttttatt ccccattgaa   1680
ctagatcaca tcttttcata ttacacactt ttatttatta taattacaca aa atg gct  1738
                                                         Met Ala
                                                          1 att aac gtt ggt att aac ggt ttc ggt aga atc ggt aga tta gtc ttg     1786
Ile Asn Val Gly Ile Asn Gly Phe Gly Arg Ile Gly Arg Leu Val Leu
       5                  10                  15 aga gtt gct tta tca aga aag gac atc aac att gtt gct gtc aat gat     1834
Arg Val Ala Leu Ser Arg Lys Asp Ile Asn Ile Val Ala Val Asn Asp
   20                  25                  30 cct ttc att gct gct gaa tac gct gct tac atg ttc aag tac gat tcc     1882
Pro Phe Ile Ala Ala Glu Tyr Ala Ala Tyr Met Phe Lys Tyr Asp Ser
35                  40                  45                  50 act cac ggt aag tac gcc ggc gaa gtt tcc agt gac ggt aaa tac tta     1930
Thr His Gly Lys Tyr Ala Gly Glu Val Ser Ser Asp Gly Lys Tyr Leu
               55                  60                  65 atc att gat ggt aag aag att gaa gtt ttc caa gaa aga gac cca gtt     1978
Ile Ile Asp Gly Lys Lys Ile Glu Val Phe Gln Glu Arg Asp Pro Val
```

-continued

```
                   70                     75                      80
aac atc cca tgg ggt aaa gaa ggt gtc caa tac gtt att gac tcc act    2026
Asn Ile Pro Trp Gly Lys Glu Gly Val Gln Tyr Val Ile Asp Ser Thr
            85                      90                      95
gtt gtt ttc act acc ttg gct ggt gct caa aag cac att gat gcc ggt    2074
Gly Val Phe Thr Thr Leu Ala Gly Ala Gln Lys His Ile Asp Ala Gly
        100                     105                     110
gct gaa aag gtt atc atc act gct cca tct gct gat gct cca atg ttc    2122
Ala Glu Lys Val Ile Ile Thr Ala Pro Ser Ala Asp Ala Pro Met Phe
115                     120                     125                     130
gtt gtt ggt gtt aac gaa aag gaa tac act tct gac ttg aag att gtt    2170
Val Val Gly Val Asn Glu Lys Glu Tyr Thr Ser Asp Leu Lys Ile Val
                135                     140                     145
tct aac gct tca tgt acc acc aac tgt ttg gct cca tta gct aag gtt    2218
Ser Asn Ala Ser Cys Thr Thr Asn Cys Leu Ala Pro Leu Ala Lys Val
            150                     155                     160
gtt aac gac aac ttt ggt att gaa tca ggt tta atg acc act gtc cac    2266
Val Asn Asp Asn Phe Gly Ile Glu Ser Gly Leu Met Thr Thr Val His
        165                     170                     175
tcc att acc gct acc caa aag acc gtc gat ggt cca tca cac aag gac    2314
Ser Ile Thr Ala Thr Gln Lys Thr Val Asp Gly Pro Ser His Lys Asp
180                     185                     190
tgg aga ggt ggt aga act gct tcc ggt aac att atc cca tca tct act    2362
Trp Arg Gly Gly Arg Thr Ala Ser Gly Asn Ile Ile Pro Ser Ser Thr
195                     200                     205                     210
ggt gct gct aag gct gtt ggt aag gtt tta cct gtc tta gct ggt aag    2410
Gly Ala Ala Lys Ala Val Gly Lys Val Leu Pro Val Leu Ala Gly Lys
                215                     220                     225
tta acc ggt atg tct tta aga gtt cct act acc gat gtt tcc gtt gtt    2458
Leu Thr Gly Met Ser Leu Arg Val Pro Thr Thr Asp Val Ser Val Val
            230                     235                     240
gat tta acc gtt aac tta aag act cca acc act tac gaa gct att tgt    2506
Asp Leu Thr Val Asn Leu Lys Thr Pro Thr Thr Tyr Glu Ala Ile Cys
        245                     250                     255
gct gct atg aag aag gct tct gaa ggt gaa tta aag ggt gtt tta ggt    2554
Ala Ala Met Lys Lys Ala Ser Glu Gly Glu Leu Lys Gly Val Leu Gly
260                     265                     270
tac act gaa gac gct gtt gtt tcc act gat ttc tta acc gat aac aga    2602
Tyr Thr Glu Asp Ala Val Val Ser Thr Asp Phe Leu Thr Asp Asn Arg
275                     280                     285                     290
tca tct atc ttt gat gct aag gct ggt atc tta tta acc cca act ttc    2650
Ser Ser Ile Phe Asp Ala Lys Ala Gly Ile Leu Leu Thr Pro Thr Phe
                295                     300                     305
gtt aag tta atc tct tgg tac gat aac gaa tac ggt tac tcc acc aga    2698
Val Lys Leu Ile Ser Trp Tyr Asp Asn Glu Tyr Gly Tyr Ser Thr Arg
            310                     315                     320
gtt gtt gat tta cta caa cac gtt gct tcc gct taa atcttacaat         2744
Val Val Asp Leu Leu Gln His Val Ala Ser Ala *
        325                     330 ctagattgtg aagtataagt aagcaaaaat tatatatata tttgtctttc atagtataag  2804
tatagttttc atgagaaata cagataaaca acaaaaaata agttcttttt gaaaagtta   2864 gattttattc ttgaacttag taaaagcctt cctttacag ctgcttactt acaaccttga   2924
aggctattgc ataagctcaa ttgaaaacga gtataatata ctgatttcaa ggtttaatta  2984
tctgtaattt tcaagtactt ccatacgtgg aaacctccca caattaacag caacacgaaa  3044
catccatcat ccaacaaccg agatgcggat taggcccgga gagataatat ttttcggtgt  3104
ggcggtggtt tcaactccga acgcagcgca gccaaaagca aacagatgat ttagtgaact  3164
```

-continued

```
cttcttatga tagatttttg gctgattgag ttgatctgac ctgtgtggtt cgatcgaatt    3224
ctattgtgtt tgatgccctg gtagtggtgt gcttcatctt attgtgaagt gtgaatccta    3284
gcgattatgg catttggacg ccaactacta gctctgacgg tagtggcttc tacgaatgta    3344
acttacaatt ctgctcaatt cgaacatctt ttcagtaaga gaagttatat atgtatgtgt    3404
gtatgtgtat gtaaatatac ataaccgctt gtggggtga tttttggttt gtactgatgt    3464
gaaactcagt gctatcggat gatgctgtca ccaacaacag ctgcttaacc ttcttttac     3524 tattctgata cagaattagg aaagtttccg gatttgtgat gtgcggcttt ggttgccatt    3584
agtctccttt ttttggaggg aggagtgaag tggtgcgtta tgtgccctga tccaatggtt    3644
ttgaaagagg gagctaggga tagttaatgg gtagacctat gaacattgtg tattaatata    3704
ttgaaatata caaacataac ggctgaaaac agcaagaaat caaaaaggca caatttcaat    3764
ggtatataac ttcaataatg atagtaatag taatggtagt agttattaca ggaggaataa    3824
tatcaagaaa ggaaaactaa aagtacacca acgtattcag aaatacaaaa acagcgaaca    3884
aaatcgtcga ttagtaattc atatcatgat tgccatccaa acagctttct ttcattgaac    3944
tcacgagggc ttgcactatt ttccctgctt gatgagtaat ccatcatttc aaactcggtt    4004
gaacctgtag caccagaagc gccatttgac gtaattggcc ttgtaatttg ctgttgttgt    4064
tgggatatgt ttgattcatt ttggaaacgt tcatgatgcc ctctttttt gttgtttgtt     4124 gttggtatcg gtgaattcga tctagatgca gaactgccac tattgttgtt attgccgttg    4184
ttcgcattat tgttatcgtc aaagtcaaag tcaagtaatg gaagaccaag ggaagcatca    4244
acaccaaaat cattcaacat cagtaaatcc gagtacgact taatggtatc tgcctgaatc    4304
gttgcttgct gctgattatg ctgttgttgg ttttgttgtt gctgtttcgc agtcagttgg    4364
aaatgatcca ctagttctag agcggccgcc accgcggtgg agctc                    4409
```

<210> SEQ ID NO 6
<211> LENGTH: 3333
<212> TYPE: DNA
<213> ORGANISM: Pichia methanolica
<220> FEATURE:
<221> NAME/KEY: CDS
<222> LOCATION: (1093)...(2094)

<400> SEQUENCE: 6

```
cataaaccat aatagtataa tttgttagac aagttcaaag aatttccaat aaaagtgtaa      60
ttttcacatg catttcaacc cggagaataa aattttaaga aatccgattg gatagtgtag     120
aattattgtt catattgtgt tataataatt gcaattaccc aacaaaactt gcattggtta     180
gtcatcgtat ttcatgctat tagctgaaag tagggtaatc gagcggtttg aatggctctg     240
taaatctaaa ctctttatct gaaatgtata ttagatccga catgatgcat ttggaggttc     300
tgagaggtac cgcattgaat ttctgtgtgg aattagatga gttgttgtac cagaagaggg     360
aaaatgggca gtggtggca atagtaaatt atgggaagta tggtggatat tggcccggcg      420
tagtgacatc ctcaccttaa aattgcctta ggggataatg tgccgggcac gtccagctaa     480
ctaatttagt agtcgtctaa aactggggaa catttgttgt tcctttgata gttatacgaa     540
actgattgaa taaaagtttt atattcttct tgatgatcct tctgtctaat tgatagaata    600
ggaatttaga tagaaatatg gaaatacaca aaatatatgt aataaaatca aaaggggaac     660
aattcaaagg attcagcaat caaagggat gagtgattct gggtaataaa tgagcaataa     720
attagtaata aattagtaac aagttagtaa taaattagta ataaattagc aacaaatgaa     780
```

-continued

```
caatagtaaa agctaaaaga taaaacaaaa ggtaggagat aagcagtaaa gtccgaaagt      840
aatcaggtga ctagagtaag gatgagaatg aaggacagat tccttacagc tacataagta      900
gatgagctgt tgacggtcag atggtgcctt ggtccatggt ttcatatata aagaccctct      960
tcgtctcctt ttgttcgctt gtttcacact caactgtttc tgattttacc ttttttcccc     1020
tgcttgattc ccccattgaa tcagatcaag tgttttcata gaacccactt ttatttattt     1080
tagttgcaca aa atg gcc att aac gtt ggt att aac ggt ttc ggg aga atc     1131
              Met Ala Ile Asn Val Gly Ile Asn Gly Phe Gly Arg Ile
                1               5                  10 ggc aga tta gtc ttg aga gtt gcc tta tcg aga aaa gac atc aac gtc       1179
Gly Arg Leu Val Leu Arg Val Ala Leu Ser Arg Lys Asp Ile Asn Val
     15                  20                  25 gtt gct gtc aac gat cct ttc att gct cct gat tac gct gct tac atg       1227
Val Ala Val Asn Asp Pro Phe Ile Ala Pro Asp Tyr Ala Ala Tyr Met
 30                  35                  40                  45 ttc aag tac gat tcc act cac ggt aag tac act ggt gaa gtt tca agt       1275
Phe Lys Tyr Asp Ser Thr His Gly Lys Tyr Thr Gly Glu Val Ser Ser
                 50                  55                  60 gat ggt aaa tac tta atc att gat ggt aag aag att gaa gtt ttc caa       1323
Asp Gly Lys Tyr Leu Ile Ile Asp Gly Lys Lys Ile Glu Val Phe Gln
             65                  70                  75 gaa aga gat cca gcc aac atc cca tgg ggg aaa gaa ggt gtt cag tac       1371
Glu Arg Asp Pro Ala Asn Ile Pro Trp Gly Lys Glu Gly Val Gln Tyr
         80                  85                  90 gtt att gaa tcc act ggc gtt ttc acc acc ttg gct ggt gct caa aag       1419
Val Ile Glu Ser Thr Gly Val Phe Thr Thr Leu Ala Gly Ala Gln Lys
     95                  100                 105 cac att gat gct ggt gcg gaa aag gtt atc atc act gct cca tct tct       1467
His Ile Asp Ala Gly Ala Glu Lys Val Ile Ile Thr Ala Pro Ser Ser
110                  115                 120                 125 gat gct cca atg ttt gtt gtt ggt gtt aac gaa aag gaa tac act cct       1515
Asp Ala Pro Met Phe Val Val Gly Val Asn Glu Lys Glu Tyr Thr Pro
                 130                 135                 140 gac ttg aag att gtt tca aat gcc tca tgt acc acc aac tgc gtg gct       1563
Asp Leu Lys Ile Val Ser Asn Ala Ser Cys Thr Thr Asn Cys Val Ala
             145                 150                 155 aca tta gct aaa gtt gtt gac gat aac ttt gga att gaa tct ggg tta       1611
Thr Leu Ala Lys Val Val Asp Asp Asn Phe Gly Ile Glu Ser Gly Leu
         160                 165                 170 atg acc gct gtt cac gcc att act gct tcc caa aag atc gtc gat ggt       1659
Met Thr Ala Val His Ala Ile Thr Ala Ser Gln Lys Ile Val Asp Gly
     175                 180                 185 ccc tcc cac aag gac tgg aga ggt ggt aga acc gct tcc ggc aac att       1707
Pro Ser His Lys Asp Trp Arg Gly Gly Arg Thr Ala Ser Gly Asn Ile
190                  195                 200                 205 atc cca tca tca act ggt gct gct aag gct gtt ggt aag gtt ttg cca       1755
Ile Pro Ser Ser Thr Gly Ala Ala Lys Ala Val Gly Lys Val Leu Pro
                 210                 215                 220 gct tta gct ggc aag cta acc ggt atg tct ata agg gtt cct act act       1803
Ala Leu Ala Gly Lys Leu Thr Gly Met Ser Ile Arg Val Pro Thr Thr
             225                 230                 235 gat gtt tcc gtt gct gat tta acc gtt aac tta aag act gct acc acc       1851
Asp Val Ser Val Ala Asp Leu Thr Val Asn Leu Lys Thr Ala Thr Thr
         240                 245                 250 tac cag gaa att tgc gct gct ata aag aag gct tct gaa ggt gaa tta       1899
Tyr Gln Glu Ile Cys Ala Ala Ile Lys Lys Ala Ser Glu Gly Glu Leu
     255                 260                 265
```

| | | | | | | | | | | | | | | |
|---|---|---|---|---|---|---|---|---|---|---|---|---|---|---|
|aag|ggt|att|tta|ggt|tac|act|gaa|gat|gcc|gtt|gtt|tca|acc|gac|ttc|1947
|Lys|Gly|Ile|Leu|Gly|Tyr|Thr|Glu|Asp|Ala|Val|Val|Ser|Thr|Asp|Phe|
|270| | | | |275| | | |280| | | | |285|

| | | | | | | | | | | | | | | | |
|---|---|---|---|---|---|---|---|---|---|---|---|---|---|---|---|
|tta|acc|gat|agc|aga|tcg|tct|atc|ttc|gat|gcc|aaa|gct|ggt|atc|tta|1995
|Leu|Thr|Asp|Ser|Arg|Ser|Ser|Ile|Phe|Asp|Ala|Lys|Ala|Gly|Ile|Leu|
| | | | |290| | | | |295| | | | |300| |

| | | | | | | | | | | | | | | | |
|---|---|---|---|---|---|---|---|---|---|---|---|---|---|---|---|
|tta|acc|cca|acc|ttc|gtt|aag|cta|atc|tct|tgg|tac|gat|aac|gaa|tac|2043
|Leu|Thr|Pro|Thr|Phe|Val|Lys|Leu|Ile|Ser|Trp|Tyr|Asp|Asn|Glu|Tyr|
| | | | |305| | | | |310| | | | |315| |

| | | | | | | | | | | | | | | | |
|---|---|---|---|---|---|---|---|---|---|---|---|---|---|---|---|
|ggt|tat|tcc|acc|aga|gtt|gtt|gac|tta|cta|caa|cat|gtt|gct|tcc|gcc|2091
|Gly|Tyr|Ser|Thr|Arg|Val|Val|Asp|Leu|Leu|Gln|His|Val|Ala|Ser|Ala|
| | | |320| | | | |325| | | | |330| | |

```
taa atcttccaac ctaaattgcg aaatataagc aagcaaaaat tatatgtata        2144
 * tttgtcttcc attgcataag tctatctttc ctgagaaata acaaaaatat gttcttttcg  2204
agacacttaa gttttatttt tgcccttagt acaaggcatc catttgcagt tgctgcttac  2264
agccctgaag gctattgcat cagcccaatt ggaaacaagt atagcatact gatttgaggg  2324
tttaattatc tgtaatattc aagtacttat atgcgtagaa cctccaaata gcaacacgaa  2384
aatccatcat ccaacaatca agatgtgga gcaggccaag caagatgata ttttctcggt   2444
ggtggcggtt tcaatttctg gggtgcgtta ttgtgtggct tgtaccttgc agggtaaacc  2504
ttcgccagca gttccagtgg tctcttcgac gaacaacagg ctgaaattcg gctgtttcag  2564
catggcttgt ttttcctcca tgggactagc gtagatttat ccccccagaa agtttctctt  2624
cttgaatatc tctggtaccg accactaact agattataga ttactgcgac atgttaaagc  2684
attgtcgggg tctttaagca tgctcaacca acaggttgcc tgaagagctg cgtactaacc  2744
tggaacaggg ttcacagaaa gagggcaacc cagaaaaaac actatttgtt aacccttata  2804
gtgaagagtg ggggtacaaa atctttgacc cgtactccac tacgacagtt ttgataaaca  2864
cttgcagatt acctaatttg gtatgtacaa tttctaggca tgggataagt atagcttta   2924 atccggaagg ttcggataaa tactgtgctg tgtgccaggc aaatgcgtcc cactggagaa  2984
aaaggtaaag ccgactaacc gaagacccac ctacaataaa tttaccgagc accgaaaaa   3044 ctcacgttac tcaatatatg agtaatgtac tactataact atgtgtggaa tagaattgta   3104
ttgtatagta gctcagcttt cttcctggta tacggtcgac tttagcctaa acacttgttg  3164
gttcagtgaa tacagcctga ttagactaaa aggtagaagg actataaagg tgtacatacg  3224
gaaatcctac tccccactta aatagacaaa acccctctaa gtgttgtttc gacgtaaagc  3284
tttgtttact gacaagcctt ggcaccgatc ccccgggctg caggaattc               3333

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide ZC18176
<220> FEATURE:
<221> NAME/KEY: variation
<222> LOCATION: 6, 9
<223> OTHER INFORMATION: n = A, T, G or C

<400> SEQUENCE: 7
aaytcncgnt gggaytaygg                                               20

<210> SEQ ID NO 8
<211> LENGTH: 20
<212> TYPE: DNA
```

```
<213> ORGANISM: Artificial Sequence
<220> FEATURE:
<223> OTHER INFORMATION: Oligonucleotide ZC18177
<220> FEATURE:
<221> NAME/KEY: variation
<222> LOCATION: 6
<223> OTHER INFORMATION: n = A, T, G or C

<400> SEQUENCE: 8
aaytcnagrt gggaytaygg                                          20

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide ZC16562

<400> SEQUENCE: 9
ccctggggca ccgtgcaagt c                                        21

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide ZC16567

<400> SEQUENCE: 10
tcctgagtta tcaaagccgt tttg                                     24

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide ZC18180
<220> FEATURE:
<221> NAME/KEY: variation
<222> LOCATION: 3, 6, 9, 12, 15
<223> OTHER INFORMATION: n = A, T, G or C

<400> SEQUENCE: 11
tgnganccng gnacnccrtg                                          20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide ZC18181
<220> FEATURE:
<221> NAME/KEY: variation
<222> LOCATION: 3, 15
<223> OTHER INFORMATION: n = A, T, G or C

<400> SEQUENCE: 12
ccngarttrt craanccrtt                                          20

<210> SEQ ID NO 13
<211> LENGTH: 1696
<212> TYPE: DNA
<213> ORGANISM: Homo sapiens
<220> FEATURE:
<221> NAME/KEY: CDS
<222> LOCATION: (69)...(806)

<400> SEQUENCE: 13
```

```
cccgaggaga ccacgctcct ggagctctgc tgtcttctca gggagactct gaggctctgt      60 tgagaatc atg ctt tgg agg cag ctc atc tat tgg caa ctg ctg gct ttg      110
         Met Leu Trp Arg Gln Leu Ile Tyr Trp Gln Leu Leu Ala Leu
          1               5                  10 ttt ttc ctc cct ttt tgc ctg tgt caa gat gaa tac atg gag tct cca      158
Phe Phe Leu Pro Phe Cys Leu Cys Gln Asp Glu Tyr Met Glu Ser Pro
 15                  20                  25                  30 caa acc gga gga cta ccc cca gac tgc agt aag tgt tgt cat gga gac      206
Gln Thr Gly Gly Leu Pro Pro Asp Cys Ser Lys Cys Cys His Gly Asp
                 35                  40                  45 tac agc ttt cga ggc tac caa ggc ccc cct ggg cca ccg ggc cct cct      254
Tyr Ser Phe Arg Gly Tyr Gln Gly Pro Pro Gly Pro Pro Gly Pro Pro
             50                  55                  60 ggc att cca gga aac cat gga aac aat ggc aac aat gga gcc act ggt      302
Gly Ile Pro Gly Asn His Gly Asn Asn Gly Asn Asn Gly Ala Thr Gly
 65                  70                  75 cat gaa gga gcc aaa ggt gag aag ggc gac aaa ggt gac ctg ggg cct      350
His Glu Gly Ala Lys Gly Glu Lys Gly Asp Lys Gly Asp Leu Gly Pro
         80                  85                  90 cga ggg gag cgg ggg cag cat ggc ccc aaa gga gag aag ggc tac ccg      398
Arg Gly Glu Arg Gly Gln His Gly Pro Lys Gly Glu Lys Gly Tyr Pro
 95                 100                 105                 110 ggg att cca cca gaa ctt cag att gca ttc atg gct tct ctg gca acc      446
Gly Ile Pro Pro Glu Leu Gln Ile Ala Phe Met Ala Ser Leu Ala Thr
                115                 120                 125 cac ttc agc aat cag aac agt ggg att atc ttc agc agt gtt gag acc      494
His Phe Ser Asn Gln Asn Ser Gly Ile Ile Phe Ser Ser Val Glu Thr
            130                 135                 140 aac att gga aac ttc ttt gat gtc atg act ggt aga ttt ggg gcc cca      542
Asn Ile Gly Asn Phe Phe Asp Val Met Thr Gly Arg Phe Gly Ala Pro
145                 150                 155 gta tca ggt gtg tat ttc ttc acc ttc agc atg atg aag cat gag gat      590
Val Ser Gly Val Tyr Phe Phe Thr Phe Ser Met Met Lys His Glu Asp
160                 165                 170 gtt gag gaa gtg tat gtg tac ctt atg cac aat ggc aac aca gtc ttc      638
Val Glu Glu Val Tyr Val Tyr Leu Met His Asn Gly Asn Thr Val Phe
175                 180                 185                 190 agc atg tac agc tat gaa atg aag ggc aaa tca gat aca tcc agc aat      686
Ser Met Tyr Ser Tyr Glu Met Lys Gly Lys Ser Asp Thr Ser Ser Asn
                195                 200                 205 cat gct gtg ctg aag cta gcc aaa ggg gat gag gtt tgg ctg cga atg      734
His Ala Val Leu Lys Leu Ala Lys Gly Asp Glu Val Trp Leu Arg Met
            210                 215                 220 ggc aat ggc gct ctc cat ggg gac cac caa cgc ttc tcc acc ttt gca      782
Gly Asn Gly Ala Leu His Gly Asp His Gln Arg Phe Ser Thr Phe Ala
225                 230                 235 gga ttc ctg ctc ttt gaa act aag taaatatatg actagaatag ctccactttg      836
Gly Phe Leu Leu Phe Glu Thr Lys
240                 245 gggaagactt gtagctgagc tgatttgtta cgatctgagg aacattaaag ttgagggttt      896
tacattgctg tattcaaaaa attattggtt gcaatgttgt tcacgctaca ggtacaccaa      956
taatgttgga caattcaggg gctcagaaga atcaaccaca aaatagtctt ctcagatgac     1016
cttgactaat atactcagca tctttatcac tctttccttg gcacctaaaa gataattctc     1076
ctctgacgca ggttggaaat atttttttct atcacagaag tcatttgcaa agaattttga     1136
ctactctgct tttaatttaa taccagtttt caggaacccc tgaagtttta agttcattat     1196
tctttataac atttgagaga atcggatgta gtgatatgac agggctgggg caagaacagg     1256
```

```
ggcactagct gccttattag ctaatttagt gccctccgtg ttcagcttag cctttgaccc    1316
tttccttttg atccacaaaa tacattaaaa ctctgaattc acatacaatg ctatttaaa     1376 gtcaatagat tttagctata aagtgcttga ccagtaatgt ggttgtaatt ttgtgtatgt    1436
tcccccacat cgcccccaac ttcggatgtg gggtcaggag gttgaggttc actattaaca    1496
aatgtcataa atatctcata gaggtacagt gccaatagat attcaaatgt tgcatgttga    1556
ccagagggat tttatatctg aagaacatac actattaata aataccttag agaaagattt    1616
tgacctggct ttagataaaa ctgtggcaag aaaaatgtaa tgagcaatat atggaaataa    1676
acacaccttt gttaaagata                                                 1696
```

<210> SEQ ID NO 14
<211> LENGTH: 246
<212> TYPE: PRT
<213> ORGANISM: Homo sapiens

<400> SEQUENCE: 14

```
Met Leu Trp Arg Gln Leu Ile Tyr Trp Gln Leu Leu Ala Leu Phe Phe
  1               5                  10                  15

Leu Pro Phe Cys Leu Cys Gln Asp Glu Tyr Met Glu Ser Pro Gln Thr
             20                  25                  30

Gly Gly Leu Pro Pro Asp Cys Ser Lys Cys Cys His Gly Asp Tyr Ser
         35                  40                  45

Phe Arg Gly Tyr Gln Gly Pro Pro Gly Pro Pro Gly Pro Pro Gly Ile
     50                  55                  60

Pro Gly Asn His Gly Asn Asn Gly Asn Asn Gly Ala Thr Gly His Glu
 65                  70                  75                  80

Gly Ala Lys Gly Glu Lys Gly Asp Lys Gly Asp Leu Gly Pro Arg Gly
                 85                  90                  95

Glu Arg Gly Gln His Gly Pro Lys Gly Glu Lys Gly Tyr Pro Gly Ile
            100                 105                 110

Pro Pro Glu Leu Gln Ile Ala Phe Met Ala Ser Leu Ala Thr His Phe
        115                 120                 125

Ser Asn Gln Asn Ser Gly Ile Ile Phe Ser Ser Val Glu Thr Asn Ile
    130                 135                 140

Gly Asn Phe Phe Asp Val Met Thr Gly Arg Phe Gly Ala Pro Val Ser
145                 150                 155                 160

Gly Val Tyr Phe Phe Thr Phe Ser Met Met Lys His Glu Asp Val Glu
                165                 170                 175

Glu Val Tyr Val Tyr Leu Met His Asn Gly Asn Thr Val Phe Ser Met
            180                 185                 190

Tyr Ser Tyr Glu Met Lys Gly Lys Ser Asp Thr Ser Ser Asn His Ala
        195                 200                 205

Val Leu Lys Leu Ala Lys Gly Asp Glu Val Trp Leu Arg Met Gly Asn
    210                 215                 220

Gly Ala Leu His Gly Asp His Gln Arg Phe Ser Thr Phe Ala Gly Phe
225                 230                 235                 240

Leu Leu Phe Glu Thr Lys
                245
```

<210> SEQ ID NO 15
<211> LENGTH: 65
<212> TYPE: DNA
<213> ORGANISM: Artificial Sequence
<220> FEATURE:

-continued

```
<223> OTHER INFORMATION: Oligonucleotide ZC37475

<400> SEQUENCE: 15
attgctgcta aagaagaagg tgtaagcttg tacaagagac aagatgaata catggagtct    60
ccaca                                                                65

<210> SEQ ID NO 16
<211> LENGTH: 68
<212> TYPE: DNA
<213> ORGANISM: Artificial Sequence
<220> FEATURE:
<223> OTHER INFORMATION: Oligonucleotide ZC37474

<400> SEQUENCE: 16
caaaaattat aaaatatcc aaacaggcag ccgaattcta ttacttagtt tcaaagagca     60
ggaatcct                                                             68

<210> SEQ ID NO 17
<211> LENGTH: 67
<212> TYPE: DNA
<213> ORGANISM: Artificial Sequence
<220> FEATURE:
<223> OTHER INFORMATION: Oligonucleotide ZC39207

<400> SEQUENCE: 17
aaaaaatctt actattaatt tctcaaaaga attcaaaaga atgaagttct cgctaagtac    60
attgaca                                                              67

<210> SEQ ID NO 18
<211> LENGTH: 63
<212> TYPE: DNA
<213> ORGANISM: Artificial Sequence
<220> FEATURE:
<223> OTHER INFORMATION: Oligonucleotide ZC39209

<400> SEQUENCE: 18
gggaccacct tccattggca tgtattcttc ttctctcttt ttcaaagtga gtggtgcagc    60
tga                                                                  63

<210> SEQ ID NO 19
<211> LENGTH: 65
<212> TYPE: DNA
<213> ORGANISM: Artificial Sequence
<220> FEATURE:
<223> OTHER INFORMATION: Oligonucleotide ZC39208

<400> SEQUENCE: 19
tcattggtct cagctgcacc actcactttg aaaaagagac aagatgaata catggagtct    60
ccaca                                                                65

<210> SEQ ID NO 20
<211> LENGTH: 754
<212> TYPE: DNA
<213> ORGANISM: Artificial Sequence
<220> FEATURE:
<223> OTHER INFORMATION: alphaFpp::zacrp3 fragment

<400> SEQUENCE: 20
attgctgcta aagaagaagg tgtatcctta tacaagagac aagatgaata catggagtct    60
ccacaaaccg gaggactacc cccagactgc agtaagtgtt gtcatggaga ctacagcttt   120
cgaggctacc aaggccccc tgggccaccg ggccctcctg gcattccagg aaaccatgga    180
```

```
aacaatggca acaatggagc cactggtcat gaaggagcca aaggtgagaa gggcgacaaa      240
ggtgacctgg ggcctcgagg ggagcggggg cagcatggcc ccaaaggaga aagggctac      300 ccggggattc caccagaact tcagattgca ttcatggctt ctctggcaac ccacttcagc      360
aatcagaaca gtgggattat cttcagcagt gttgagacca acattggaaa cttctttgat      420
gtcatgactg gtagatttgg ggccccagta tcaggtgtgt atttcttcac cttcagcatg      480
atgaagcatg aggatgttga ggaagtgtat gtgtacctta tgcacaatgg caacacagtc      540
ttcagcatgt acagctatga aatgaagggc aaatcagata catccagcaa tcatgctgtg      600
ctgaagctag ccaaggggga tgaggtttgg ctgcgaatgg gcaatggcgc tctccatggg      660
gaccaccaac gcttctccac ctttgcagga ttcctgctct ttgaaactaa gtaatagaat      720
tcggctgcct gtttggatat ttttataatt tttg                                  754

<210> SEQ ID NO 21
<211> LENGTH: 157
<212> TYPE: DNA
<213> ORGANISM: Pichia methanolica

<400> SEQUENCE: 21
aaaaaatctt actattaatt tctcaaaaga attcaaaaga atgaagttct cgctaagtac       60
attgacagtt atcaccacct tactatcatt ggtctcagct gcaccactca ctttgaaaaa      120
gagagaagaa gaatacatgc caatggaagg tggtccc                               157

<210> SEQ ID NO 22
<211> LENGTH: 754
<212> TYPE: DNA
<213> ORGANISM: Homo sapiens

<400> SEQUENCE: 22
tcattggtct cagctgcacc actcactttg aaaagagac aagatgaata catggagtct        60
ccacaaaccg gaggactacc cccagactgc agtaagtgtt gtcatggaga ctacagcttt      120
cgaggctacc aaggcccccc tgggccaccg ggccctcctg gcattccagg aaaccatgga      180
aacaatggca acaatggagc cactggtcat gaaggagcca aaggtgagaa gggcgacaaa      240
ggtgacctgg ggcctcgagg ggagcggggg cagcatggcc ccaaaggaga aagggctac      300 ccggggattc caccagaact tcagattgca ttcatggctt ctctggcaac ccacttcagc      360
aatcagaaca gtgggattat cttcagcagt gttgagacca acattggaaa cttctttgat      420
gtcatgactg gtagatttgg ggccccagta tcaggtgtgt atttcttcac cttcagcatg      480
atgaagcatg aggatgttga ggaagtgtat gtgtacctta tgcacaatgg caacacagtc      540
ttcagcatgt acagctatga aatgaagggc aaatcagata catccagcaa tcatgctgtg      600
ctgaagctag ccaaggggga tgaggtttgg ctgcgaatgg gcaatggcgc tctccatggg      660
gaccaccaac gcttctccac ctttgcagga ttcctgctct ttgaaactaa gtaatagaat      720
tcggctgcct gtttggatat ttttataatt tttg                                  754

<210> SEQ ID NO 23
<211> LENGTH: 930
<212> TYPE: DNA
<213> ORGANISM: Artificial Sequence
<220> FEATURE:
<223> OTHER INFORMATION: pSDH147

<400> SEQUENCE: 23
```

```
atgagatttc cttctatttt tactgctgtt ttattcgctg cttcctccgc tttagctgct    60
ccagtcaaca ctaccactga agatgaaacg gctcaaattc cagctgaagc tgtcatcggt   120
tactctgatt tagaaggtga tttcgatgtt gctgttttgc catttccaa ctccaccaat   180
aacggtttat tgtttatcaa tactactatt gctagcattg ctgctaaaga agaaggtgta   240
tccttataca agagacaaga tgaatacatg gagtctccac aaaccggagg actaccccca   300
gactgcagta agtgttgtca tggagactac agctttcgag ctaccaagg ccccctggg    360
ccaccgggcc ctcctggcat tccaggaaac catggaaaca atggcaacaa tggagccact   420
ggtcatgaag gagccaaagg tgagaagggc gacaaaggtg acctgggcc tcgaggggag    480
cgggggcagc atggccccaa aggagagaag ggctacccgg ggattccacc agaacttcag   540
attgcattca tggcttctct ggcaacccac ttcagcaatc agaacagtgg gattatcttc   600
agcagtgttg agaccaacat tggaaacttc tttgatgtca tgactggtag atttggggcc   660
ccagtatcag gtgtgtattt cttcaccttc agcatgatga agcatgagga tgttgaggaa   720
gtgtatgtgt accttatgca aatggcaac acagtcttca gcatgtacag ctatgaaatg   780
aaggcaaat cagatacatc cagcaatcat gctgtgctga agctagccaa aggggatgag   840
gtttggctgc gaatgggcaa tggcgctctc catggggacc accaacgctt ctccaccttt   900
gcaggattcc tgctctttga aactaagtaa                                     930
```

<210> SEQ ID NO 24
<211> LENGTH: 309
<212> TYPE: PRT
<213> ORGANISM: Artificial Sequence
<220> FEATURE:
<223> OTHER INFORMATION: pSDH147

<400> SEQUENCE: 24

```
Met Arg Phe Pro Ser Ile Phe Thr Ala Val Leu Phe Ala Ala Ser Ser
  1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Leu Tyr Lys Arg Gln Asp Glu Tyr Met Glu Ser Pro Gln Thr Gly
                 85                  90                  95

Gly Leu Pro Pro Asp Cys Ser Lys Cys Cys His Gly Asp Tyr Ser Phe
            100                 105                 110

Arg Gly Tyr Gln Gly Pro Pro Gly Pro Pro Gly Pro Pro Gly Ile Pro
        115                 120                 125

Gly Asn His Gly Asn Asn Gly Asn Asn Gly Ala Thr Gly His Glu Gly
    130                 135                 140

Ala Lys Gly Glu Lys Gly Asp Lys Gly Asp Leu Gly Pro Arg Gly Glu
145                 150                 155                 160

Arg Gly Gln His Gly Pro Lys Gly Glu Lys Gly Tyr Pro Gly Ile Pro
                165                 170                 175

Pro Glu Leu Gln Ile Ala Phe Met Ala Ser Leu Ala Thr His Phe Ser
            180                 185                 190

Asn Gln Asn Ser Gly Ile Ile Phe Ser Ser Val Glu Thr Asn Ile Gly
```

```
                195                 200                 205
Asn Phe Phe Asp Val Met Thr Gly Arg Phe Gly Ala Pro Val Ser Gly
    210                 215                 220

Val Tyr Phe Phe Thr Phe Ser Met Met Lys His Glu Asp Val Glu Glu
225                 230                 235                 240

Val Tyr Val Tyr Leu Met His Asn Gly Asn Thr Val Phe Ser Met Tyr
                245                 250                 255

Ser Tyr Glu Met Lys Gly Lys Ser Asp Thr Ser Asn His Ala Val
            260                 265                 270

Leu Lys Leu Ala Lys Gly Asp Glu Val Trp Leu Arg Met Gly Asn Gly
        275                 280                 285

Ala Leu His Gly Asp His Gln Arg Phe Ser Thr Phe Ala Gly Phe Leu
    290                 295                 300

Leu Phe Glu Thr Lys
305

<210> SEQ ID NO 25
<211> LENGTH: 759
<212> TYPE: DNA
<213> ORGANISM: Artificial Sequence
<220> FEATURE:
<223> OTHER INFORMATION: pSDH149

<400> SEQUENCE: 25
atgaagttct cgctaagtac attgacagtt atcaccacct tactatcatt ggtctcagct       60
gcaccactca ctttgaaaaa gagacaagat gaatacatgg agtctccaca aaccggagga     120 ctaccccag actgcagtaa gtgttgtcat ggagactaca gctttcgagg ctaccaaggc      180 cccctgggc accgggccc tcctggcatt ccaggaaacc atggaaacaa tgcaacaat       240 ggagccactg gtcatgaagg agccaaaggt gagaagggcg acaaggtga cctggggcct     300 cgaggggagc gggggcagca tggccccaaa ggagagaagg gctacccggg gattccacca    360
gaacttcaga ttgcattcat ggcttctctg caaccccact tcagcaatca gaacagtggg    420
attatcttca gcagtgttga gaccaacatt ggaaacttct tgatgtcat gactggtaga     480 tttgggccc cagtatcagg tgtgtatttc ttcaccttca gcatgatgaa gcatgaggat     540
gttgaggaag tgtatgtgta ccttatgcac aatggcaaca cagtcttcag catgtacagc    600
tatgaaatga agggcaaatc agatacatcc agcaatcatg ctgtgctgaa gctagccaaa    660
ggggatgagg tttggctgcg aatgggcaat ggcgctctcc atggggacca ccaacgcttc    720
tccacctttg caggattcct gctctttgaa actaagtaa                            759

<210> SEQ ID NO 26
<211> LENGTH: 252
<212> TYPE: PRT
<213> ORGANISM: Artificial Sequence
<220> FEATURE:
<223> OTHER INFORMATION: pSDH149

<400> SEQUENCE: 26

Met Lys Phe Ser Leu Ser Thr Leu Thr Val Ile Thr Thr Leu Leu Ser
  1               5                  10                  15

Leu Val Ser Ala Ala Pro Leu Thr Leu Lys Lys Arg Gln Asp Glu Tyr
                20                  25                  30

Met Glu Ser Pro Gln Thr Gly Gly Leu Pro Pro Asp Cys Ser Lys Cys
            35                  40                  45

Cys His Gly Asp Tyr Ser Phe Arg Gly Tyr Gln Gly Pro Pro Gly Pro
```

```
                50                  55                  60
Pro Gly Pro Gly Ile Pro Gly Asn His Gly Asn Asn Gly Asn Asn
 65                  70                  75                  80

Gly Ala Thr Gly His Glu Gly Ala Lys Gly Glu Lys Gly Asp Lys Gly
                 85                  90                  95

Asp Leu Gly Pro Arg Gly Glu Arg Gly Gln His Gly Pro Lys Gly Glu
            100                 105                 110

Lys Gly Tyr Pro Gly Ile Pro Pro Glu Leu Gln Ile Ala Phe Met Ala
        115                 120                 125

Ser Leu Ala Thr His Phe Ser Asn Gln Asn Ser Gly Ile Ile Phe Ser
    130                 135                 140

Ser Val Glu Thr Asn Ile Gly Asn Phe Phe Asp Val Met Thr Gly Arg
145                 150                 155                 160

Phe Gly Ala Pro Val Ser Gly Val Tyr Phe Thr Phe Ser Met Met
                165                 170                 175

Lys His Glu Asp Val Glu Val Tyr Val Tyr Leu Met His Asn Gly
                180                 185                 190

Asn Thr Val Phe Ser Met Tyr Ser Tyr Glu Met Lys Gly Lys Ser Asp
            195                 200                 205

Thr Ser Asn His Ala Val Leu Lys Leu Ala Lys Gly Asp Glu Val
    210                 215                 220

Trp Leu Arg Met Gly Asn Gly Ala Leu His Gly Asp His Gln Arg Phe
225                 230                 235                 240

Ser Thr Phe Ala Gly Phe Leu Leu Phe Glu Thr Lys
                245                 250
```

<210> SEQ ID NO 27
<211> LENGTH: 1026
<212> TYPE: DNA
<213> ORGANISM: Homo sapiens
<220> FEATURE:
<221> NAME/KEY: CDS
<222> LOCATION: (1)...(1026)

<400> SEQUENCE: 27

```
atg aga ttt cct tct att ttt act gct gtt tta ttc gct gct tcc tcc      48
Met Arg Phe Pro Ser Ile Phe Thr Ala Val Leu Phe Ala Ala Ser Ser
 1               5                  10                  15 gct tta gct gct cca gtc aac act acc act gaa gat gaa acg gct caa      96
Ala Leu Ala Ala Pro Val Asn Thr Thr Thr Glu Asp Glu Thr Ala Gln
             20                  25                  30 att cca gct gaa gct gtc atc ggt tac tct gat tta gaa ggt gat ttc     144
Ile Pro Ala Glu Ala Val Ile Gly Tyr Ser Asp Leu Glu Gly Asp Phe
         35                  40                  45 gat gtt gct gtt ttg cca ttt tcc aac tcc acc aat aac ggt tta ttg     192
Asp Val Ala Val Leu Pro Phe Ser Asn Ser Thr Asn Asn Gly Leu Leu
     50                  55                  60 ttt atc aat act act att gct agc att gct gct aaa gaa gaa ggt gta     240
Phe Ile Asn Thr Thr Ile Ala Ser Ile Ala Ala Lys Glu Glu Gly Val
 65                  70                  75                  80 agc ttg tac aag aga aga gtt cct cat gtc caa ggt gaa caa caa gag     288
Ser Leu Tyr Lys Arg Arg Val Pro His Val Gln Gly Glu Gln Gln Glu
             85                  90                  95 tgg gag ggt act gag gag ttg cca tcc cct cca gac cat gcc gag aga     336
Trp Glu Gly Thr Glu Glu Leu Pro Ser Pro Pro Asp His Ala Glu Arg
        100                 105                 110 gct gaa gaa caa cat gaa aaa tac aga cca tct caa gac caa ggt ttg     384
Ala Glu Glu Gln His Glu Lys Tyr Arg Pro Ser Gln Asp Gln Gly Leu
```

```
                115                 120                 125
cct gct tcc aga tgc ttg aga tgc tgt gac cct ggt acc tcc atg tac        432
Pro Ala Ser Arg Cys Leu Arg Cys Cys Asp Pro Gly Thr Ser Met Tyr
        130                 135                 140 cca gct acc gcc gtt cca caa atc aac atc act atc ttg aaa ggt gag        480
Pro Ala Thr Ala Val Pro Gln Ile Asn Ile Thr Ile Leu Lys Gly Glu
145                 150                 155                 160 aag ggt gac aga gga gat aga ggc ttg caa ggt aag tat ggc aaa aca        528
Lys Gly Asp Arg Gly Asp Arg Gly Leu Gln Gly Lys Tyr Gly Lys Thr
                165                 170                 175 ggc tca gca ggt gcc aga ggc cac act ggt cca aaa ggt caa aag ggc        576
Gly Ser Ala Gly Ala Arg Gly His Thr Gly Pro Lys Gly Gln Lys Gly
        180                 185                 190 tcc atg ggt gcc cct ggt gag aga tgc aag tcc cac tac gcc gcc ttt        624
Ser Met Gly Ala Pro Gly Glu Arg Cys Lys Ser His Tyr Ala Ala Phe
                195                 200                 205 tct gtt ggc aga aag aag cca atg cac tcc aac cac tac tac caa act        672
Ser Val Gly Arg Lys Lys Pro Met His Ser Asn His Tyr Tyr Gln Thr
210                 215                 220 gtt atc ttc gac act gag ttc gtt aac ttg tac gac cac ttc aac atg        720
Val Ile Phe Asp Thr Glu Phe Val Asn Leu Tyr Asp His Phe Asn Met
225                 230                 235                 240 ttc acc ggc aag ttc tac tgc tac gtt cca ggc ttg tac ttc ttc tct        768
Phe Thr Gly Lys Phe Tyr Cys Tyr Val Pro Gly Leu Tyr Phe Phe Ser
                245                 250                 255 ttg aac gtt cac acc tgg aac caa aag gag acc tac ctg cac atc atg        816
Leu Asn Val His Thr Trp Asn Gln Lys Glu Thr Tyr Leu His Ile Met
        260                 265                 270 aag aac gag gag gag gtt gtt atc ttg ttc gct caa gtt ggc gac aga        864
Lys Asn Glu Glu Glu Val Val Ile Leu Phe Ala Gln Val Gly Asp Arg
                275                 280                 285 tct atc atg caa tct caa tct ttg atg ctt gag ttg aga gag caa gac        912
Ser Ile Met Gln Ser Gln Ser Leu Met Leu Glu Leu Arg Glu Gln Asp
        290                 295                 300 caa gtt tgg gtt aga ttg tac aag ggc gaa cgt gag aac gcc atc ttc        960
Gln Val Trp Val Arg Leu Tyr Lys Gly Glu Arg Glu Asn Ala Ile Phe
305                 310                 315                 320 tct gag gag ttg gac acc tac atc acc ttc tct ggc tac ttg gtc aag       1008
Ser Glu Glu Leu Asp Thr Tyr Ile Thr Phe Ser Gly Tyr Leu Val Lys
                325                 330                 335 cac gcc acc gag cca tag                                                1026
His Ala Thr Glu Pro  *
        340

<210> SEQ ID NO 28
<211> LENGTH: 341
<212> TYPE: PRT
<213> ORGANISM: Homo sapiens

<400> SEQUENCE: 28

Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
```

```
                65                  70                  75                  80
Ser Leu Tyr Lys Arg Arg Val Pro His Val Gln Gly Glu Gln Gln Glu
                    85                  90                  95

Trp Glu Gly Thr Glu Glu Leu Pro Ser Pro Pro Asp His Ala Glu Arg
                100                 105                 110

Ala Glu Glu Gln His Glu Lys Tyr Arg Pro Ser Gln Asp Gln Gly Leu
                115                 120                 125

Pro Ala Ser Arg Cys Leu Arg Cys Cys Asp Pro Gly Thr Ser Met Tyr
    130                 135                 140

Pro Ala Thr Ala Val Pro Gln Ile Asn Ile Thr Ile Leu Lys Gly Glu
145                 150                 155                 160

Lys Gly Asp Arg Gly Asp Arg Gly Leu Gln Gly Lys Tyr Gly Lys Thr
                165                 170                 175

Gly Ser Ala Gly Ala Arg Gly His Thr Gly Pro Lys Gly Gln Lys Gly
                180                 185                 190

Ser Met Gly Ala Pro Gly Glu Arg Cys Lys Ser His Tyr Ala Ala Phe
                195                 200                 205

Ser Val Gly Arg Lys Lys Pro Met His Ser Asn His Tyr Tyr Gln Thr
    210                 215                 220

Val Ile Phe Asp Thr Glu Phe Val Asn Leu Tyr Asp His Phe Asn Met
225                 230                 235                 240

Phe Thr Gly Lys Phe Tyr Cys Tyr Val Pro Gly Leu Tyr Phe Phe Ser
                245                 250                 255

Leu Asn Val His Thr Trp Asn Gln Lys Glu Thr Tyr Leu His Ile Met
                260                 265                 270

Lys Asn Glu Glu Glu Val Val Ile Leu Phe Ala Gln Val Gly Asp Arg
                275                 280                 285

Ser Ile Met Gln Ser Gln Ser Leu Met Leu Glu Leu Arg Glu Gln Asp
    290                 295                 300

Gln Val Trp Val Arg Leu Tyr Lys Gly Glu Arg Glu Asn Ala Ile Phe
305                 310                 315                 320

Ser Glu Glu Leu Asp Thr Tyr Ile Thr Phe Ser Gly Tyr Leu Val Lys
                325                 330                 335

His Ala Thr Glu Pro
            340

<210> SEQ ID NO 29
<211> LENGTH: 64
<212> TYPE: DNA
<213> ORGANISM: Artificial Sequence
<220> FEATURE:
<223> OTHER INFORMATION: ZG42,210 primer

<400> SEQUENCE: 29
attgctgcta agaagaagg tgtaagcttg tacaagagaa gagttcctca tgtccaaggt      60
gaac                                                                 64

<210> SEQ ID NO 30
<211> LENGTH: 61
<212> TYPE: DNA
<213> ORGANISM: Artificial Sequence
<220> FEATURE:
<223> OTHER INFORMATION: ZG42,206 primer

<400> SEQUENCE: 30
aaatatccaa acaggcagcc ctagaatact aggaattcta tggctcggtg gcgtgcttga      60
``` c                                                              61

<210> SEQ ID NO 31
<211> LENGTH: 67
<212> TYPE: DNA
<213> ORGANISM: Artificial Sequence
<220> FEATURE:
<223> OTHER INFORMATION: ZG42,209 primer

<400> SEQUENCE: 31
aaaaaatctt actattaatt tctcaaaaga attcaaaaga atgaagttct cgctaagtac     60
attgaca                                                              67

<210> SEQ ID NO 32
<211> LENGTH: 64
<212> TYPE: DNA
<213> ORGANISM: Artificial Sequence
<220> FEATURE:
<223> OTHER INFORMATION: ZG42,211 primer

<400> SEQUENCE: 32
gttcaccttg gacatgagga actcttctct ttttcaaagt gagtggtgca gctgagacca     60
atga                                                                 64

<210> SEQ ID NO 33
<211> LENGTH: 64
<212> TYPE: DNA
<213> ORGANISM: Artificial Sequence
<220> FEATURE:
<223> OTHER INFORMATION: ZG42,273 primer

<400> SEQUENCE: 33
tcattggtct cagctgcacc actcactttg aaaagagaa gagttcctca tgtccaaggt     60
gaac                                                                 64

<210> SEQ ID NO 34
<211> LENGTH: 847
<212> TYPE: DNA
<213> ORGANISM: Artificial Sequence
<220> FEATURE:
<223> OTHER INFORMATION: zsig37 sequence amplified with ZG42,210 + ZG42,
    206 (pSDH156, or aFpp::zsig37)

<400> SEQUENCE: 34
attgctgcta aagaagaagg tgtaagcttg tacaagagaa gagttcctca tgtccaaggt     60
gaacaacaag agtgggaggg tactgaggag ttgccatccc ctccagacca tgccgagaga    120
gctgaagaac aacatgaaaa atacagacca tctcaagacc aaggtttgcc tgcttccaga    180
tgcttgagat gctgtgaccc tggtacctcc atgtacccag ctaccgccgt tccacaaatc    240
aacatcacta tcttgaaagg tgagaagggt gacagaggag atagaggctt gcaaggtaag    300
tatggcaaaa caggctcagc aggtgccaga ggccacactg gtccaaaagg tcaaaagggc    360
tccatgggtg ccctggtga gagatgcaag tcccactacg ccgccttttc tgttggcaga    420
aagaagccaa tgcactccaa ccactactac caaactgtta tcttcgacac tgagttcgtt    480
aacttgtacg accacttcaa catgttcacc ggcaagttct actgctacgt tccaggcttg    540
tacttcttct ctttgaacgt tcacacctgg aaccaaaagg agacctacct gcacatcatg    600
aagaacgagg aggaggttgt tatcttgttc gctcaagttg cgacagatc tatcatgcaa    660 tctcaatctt tgatgcttga gttgagagag caagaccaag tttgggttag attgtacaag    720

```
ggcgaacgtg agaacgccat cttctctgag gagttggaca cctacatcac cttctctggc      780
tacttggtca agcacgccac cgagccatag aattcctagt attctagggc tgcctgtttg      840
gatattt                                                                847
```

<210> SEQ ID NO 35
<211> LENGTH: 1026
<212> TYPE: DNA
<213> ORGANISM: Artificial Sequence
<220> FEATURE:
<223> OTHER INFORMATION: alphaFpp::zsig37 full-length nucleotide
sequence (pSDH156)
<220> FEATURE:
<221> NAME/KEY: CDS
<222> LOCATION: (1)...(1026)

<400> SEQUENCE: 35

```
atg aga ttt cct tct att ttt act gct gtt tta ttc gct gct tcc tcc      48
Met Arg Phe Pro Ser Ile Phe Thr Ala Val Leu Phe Ala Ala Ser Ser
1               5                   10                  15 gct tta gct gct cca gtc aac act acc act gaa gat gaa acg gct caa      96
Ala Leu Ala Ala Pro Val Asn Thr Thr Thr Glu Asp Glu Thr Ala Gln
            20                  25                  30 att cca gct gaa gct gtc atc ggt tac tct gat tta gaa ggt gat ttc     144
Ile Pro Ala Glu Ala Val Ile Gly Tyr Ser Asp Leu Glu Gly Asp Phe
        35                  40                  45 gat gtt gct gtt ttg cca ttt tcc aac tcc acc aat aac ggt tta ttg     192
Asp Val Ala Val Leu Pro Phe Ser Asn Ser Thr Asn Asn Gly Leu Leu
    50                  55                  60 ttt atc aat act act att gct agc att gct gct aaa gaa gaa ggt gta     240
Phe Ile Asn Thr Thr Ile Ala Ser Ile Ala Ala Lys Glu Glu Gly Val
65                  70                  75                  80 agc ttg tac aag aga aga gtt cct cat gtc caa ggt gaa caa caa gag     288
Ser Leu Tyr Lys Arg Arg Val Pro His Val Gln Gly Glu Gln Gln Glu
                85                  90                  95 tgg gag ggt act gag gag ttg cca tcc cct cca gac cat gcc gag aga     336
Trp Glu Gly Thr Glu Glu Leu Pro Ser Pro Pro Asp His Ala Glu Arg
            100                 105                 110 gct gaa gaa caa cat gaa aaa tac aga cca tct caa gac caa ggt ttg     384
Ala Glu Glu Gln His Glu Lys Tyr Arg Pro Ser Gln Asp Gln Gly Leu
        115                 120                 125 cct gct tcc aga tgc ttg aga tgc tgt gac cct ggt acc tcc atg tac     432
Pro Ala Ser Arg Cys Leu Arg Cys Cys Asp Pro Gly Thr Ser Met Tyr
    130                 135                 140 cca gct acc gcc gtt cca caa atc aac atc act atc ttg aaa ggt gag     480
Pro Ala Thr Ala Val Pro Gln Ile Asn Ile Thr Ile Leu Lys Gly Glu
145                 150                 155                 160 aag ggt gac aga gga gat aga ggc ttg caa ggt aag tat ggc aaa aca     528
Lys Gly Asp Arg Gly Asp Arg Gly Leu Gln Gly Lys Tyr Gly Lys Thr
                165                 170                 175 ggc tca gca ggt gcc aga ggc cac act ggt cca aaa ggt caa aag ggc     576
Gly Ser Ala Gly Ala Arg Gly His Thr Gly Pro Lys Gly Gln Lys Gly
            180                 185                 190 tcc atg ggt gcc cct ggt gag aga tgc aag tcc cac tac gcc gcc ttt     624
Ser Met Gly Ala Pro Gly Glu Arg Cys Lys Ser His Tyr Ala Ala Phe
        195                 200                 205 tct gtt ggc aga aag aag cca atg cac tcc aac cac tac tac caa act     672
Ser Val Gly Arg Lys Lys Pro Met His Ser Asn His Tyr Tyr Gln Thr
    210                 215                 220 gtt atc ttc gac act gag ttc gtt aac ttg tac gac cac ttc aac atg     720
Val Ile Phe Asp Thr Glu Phe Val Asn Leu Tyr Asp His Phe Asn Met
225                 230                 235                 240
```

```
ttc acc ggc aag ttc tac tgc tac gtt cca ggc ttg tac ttc ttc tct        768
Phe Thr Gly Lys Phe Tyr Cys Tyr Val Pro Gly Leu Tyr Phe Phe Ser
            245                 250                 255 ttg aac gtt cac acc tgg aac caa aag gag acc tac ctg cac atc atg        816
Leu Asn Val His Thr Trp Asn Gln Lys Glu Thr Tyr Leu His Ile Met
        260                 265                 270 aag aac gag gag gag gtt gtt atc ttg ttc gct caa gtt ggc gac aga        864
Lys Asn Glu Glu Glu Val Val Ile Leu Phe Ala Gln Val Gly Asp Arg
    275                 280                 285 tct atc atg caa tct caa tct ttg atg ctt gag ttg aga gag caa gac        912
Ser Ile Met Gln Ser Gln Ser Leu Met Leu Glu Leu Arg Glu Gln Asp
290                 295                 300 caa gtt tgg gtt aga ttg tac aag ggc gaa cgt gag aac gcc atc ttc        960
Gln Val Trp Val Arg Leu Tyr Lys Gly Glu Arg Glu Asn Ala Ile Phe
305                 310                 315                 320 tct gag gag ttg gac acc tac atc acc ttc tct ggc tac ttg gtc aag       1008
Ser Glu Glu Leu Asp Thr Tyr Ile Thr Phe Ser Gly Tyr Leu Val Lys
                325                 330                 335 cac gcc acc gag cca tag                                                1026
His Ala Thr Glu Pro *
            340

<210> SEQ ID NO 36
<211> LENGTH: 341
<212> TYPE: PRT
<213> ORGANISM: Artificial Sequence
<220> FEATURE:
<223> OTHER INFORMATION: b-glucanase::zsig37 full nucleotide sequence
      (pSDH160)

<400> SEQUENCE: 36

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Tyr Lys Arg Arg Val Pro His Val Gln Gly Glu Gln Gln Glu
                85                  90                  95

Trp Glu Gly Thr Glu Glu Leu Pro Ser Pro Pro Asp His Ala Glu Arg
            100                 105                 110

Ala Glu Glu Gln His Glu Lys Tyr Arg Pro Ser Gln Asp Gln Gly Leu
        115                 120                 125

Pro Ala Ser Arg Cys Leu Arg Cys Cys Asp Pro Gly Thr Ser Met Tyr
    130                 135                 140

Pro Ala Thr Ala Val Pro Gln Ile Asn Ile Thr Ile Leu Lys Gly Glu
145                 150                 155                 160

Lys Gly Asp Arg Gly Asp Arg Gly Leu Gln Gly Lys Tyr Gly Lys Thr
                165                 170                 175

Gly Ser Ala Gly Ala Arg Gly His Thr Gly Pro Lys Gly Gln Lys Gly
            180                 185                 190

Ser Met Gly Ala Pro Gly Glu Arg Cys Lys Ser His Tyr Ala Ala Phe
        195                 200                 205
```

```
Ser Val Gly Arg Lys Lys Pro Met His Ser Asn His Tyr Tyr Gln Thr
    210                 215                 220
Val Ile Phe Asp Thr Glu Phe Val Asn Leu Tyr Asp His Phe Asn Met
225                 230                 235                 240
Phe Thr Gly Lys Phe Tyr Cys Tyr Val Pro Gly Leu Tyr Phe Phe Ser
                245                 250                 255
Leu Asn Val His Thr Trp Asn Gln Lys Glu Thr Tyr Leu His Ile Met
            260                 265                 270
Lys Asn Glu Glu Glu Val Val Ile Leu Phe Ala Gln Val Gly Asp Arg
        275                 280                 285
Ser Ile Met Gln Ser Gln Ser Leu Met Leu Glu Leu Arg Glu Gln Asp
    290                 295                 300
Gln Val Trp Val Arg Leu Tyr Lys Gly Glu Arg Glu Asn Ala Ile Phe
305                 310                 315                 320
Ser Glu Glu Leu Asp Thr Tyr Ile Thr Phe Ser Gly Tyr Leu Val Lys
                325                 330                 335
His Ala Thr Glu Pro
            340

<210> SEQ ID NO 37
<211> LENGTH: 149
<212> TYPE: DNA
<213> ORGANISM: Artificial Sequence
<220> FEATURE:
<223> OTHER INFORMATION: b-glucanase sequence amplified with ZG42,209 +
      ZG42,211 (b-blucanase::zsig37)

<400> SEQUENCE: 37
aaaaaatctt actattaatt tctcaaaaga attcaaaaga atgaagttct cgctaagtac      60
attgacagtt atcaccacct tactatcatt ggtctcagct gcaccactca ctttgaaaaa     120
gagaagagtt cctcatgtcc aaggtgaac                                       149

<210> SEQ ID NO 38
<211> LENGTH: 847
<212> TYPE: DNA
<213> ORGANISM: Artificial Sequence
<220> FEATURE:
<223> OTHER INFORMATION: zsig37 sequence amplified with ZG42,273 + ZG42,
      206 (b-glucanase::zsig37)

<400> SEQUENCE: 38
tcattggtct cagctgcacc actcactttg aaaagagaa gagttcctca tgtccaaggt       60
gaacaacaag agtgggaggg tactgaggag ttgccatccc ctccagacca tgccgagaga     120
gctgaagaac aacatgaaaa atacagacca tctcaagacc aaggtttgcc tgcttccaga     180
tgcttgagat gctgtgaccc tggtacctcc atgtacccag ctaccgccgt tccacaaatc     240
aacatcacta tcttgaaagg tgagaagggt gacagaggag atagaggctt gcaaggtaag     300
tatggcaaaa caggctcagc aggtgccaga ggccacactg gtccaaaagg tcaaaagggc     360
tccatgggtg cccctggtga gatgcaagt cccactacg ccgccttttc tgttggcaga     420 agaagccaa tgcactccaa ccactactac caaactgtta tcttcgacac tgagttcgtt     480
aacttgtacg accacttcaa catgttcacc ggcaagttct actgctacgt tccaggcttg     540
tacttcttct ctttgaacgt tcacacctgg aaccaaaagg agacctacct gcacatcatg     600
aagaacgagg aggaggttgt tatcttgttc gctcaagttg gcgacagatc tatcatgcaa     660
tctcaatctt tgatgcttga gttgagagag caagaccaag tttgggttag attgtacaag     720
```

-continued

```
ggcgaacgtg agaacgccat cttctctgag gagttggaca cctacatcac cttctctggc      780
tacttggtca agcacgccac cgagccatag aattcctagt attctagggc tgcctgtttg      840
gatattt                                                                847
```

```
<210> SEQ ID NO 39
<211> LENGTH: 855
<212> TYPE: DNA
<213> ORGANISM: Artificial Sequence
<220> FEATURE:
<223> OTHER INFORMATION: b-glucanase::zsig37 full nucleotide sequence
      (pSDH160)
<220> FEATURE:
<221> NAME/KEY: CDS
<222> LOCATION: (1)...(855)

<400> SEQUENCE: 39
```

| | | | | | | | | | | | | | | | | |
|---|---|---|---|---|---|---|---|---|---|---|---|---|---|---|---|---|
| atg | aag | ttc | tcg | cta | agt | aca | ttg | aca | gtt | atc | acc | acc | tta | cta | tca | 48 |
| Met | Lys | Phe | Ser | Leu | Ser | Thr | Leu | Thr | Val | Ile | Thr | Thr | Leu | Leu | Ser | |
| 1 | | | | 5 | | | | | 10 | | | | | 15 | | |
| ttg | gtc | tca | gct | gca | cca | ctc | act | ttg | aaa | aag | aga | aga | gtt | cct | cat | 96 |
| Leu | Val | Ser | Ala | Ala | Pro | Leu | Thr | Leu | Lys | Lys | Arg | Arg | Val | Pro | His | |
| | | | 20 | | | | | 25 | | | | | 30 | | | |
| gtc | caa | ggt | gaa | caa | caa | gag | tgg | gag | ggt | act | gag | gag | ttg | cca | tcc | 144 |
| Val | Gln | Gly | Glu | Gln | Gln | Glu | Trp | Glu | Gly | Thr | Glu | Glu | Leu | Pro | Ser | |
| | 35 | | | | | 40 | | | | | 45 | | | | | |
| cct | cca | gac | cat | gcc | gag | aga | gct | gaa | gaa | caa | cat | gaa | aaa | tac | aga | 192 |
| Pro | Pro | Asp | His | Ala | Glu | Arg | Ala | Glu | Glu | Gln | His | Glu | Lys | Tyr | Arg | |
| 50 | | | | | 55 | | | | | 60 | | | | | | |
| cca | tct | caa | gac | caa | ggt | ttg | cct | gct | tcc | aga | tgc | ttg | aga | tgc | tgt | 240 |
| Pro | Ser | Gln | Asp | Gln | Gly | Leu | Pro | Ala | Ser | Arg | Cys | Leu | Arg | Cys | Cys | |
| 65 | | | | | 70 | | | | | 75 | | | | | 80 | |
| gac | cct | ggt | acc | tcc | atg | tac | cca | gct | acc | gcc | gtt | cca | caa | atc | aac | 288 |
| Asp | Pro | Gly | Thr | Ser | Met | Tyr | Pro | Ala | Thr | Ala | Val | Pro | Gln | Ile | Asn | |
| | | | | 85 | | | | | 90 | | | | | 95 | | |
| atc | act | atc | ttg | aaa | ggt | gag | aag | ggt | gac | aga | gga | gat | aga | ggc | ttg | 336 |
| Ile | Thr | Ile | Leu | Lys | Gly | Glu | Lys | Gly | Asp | Arg | Gly | Asp | Arg | Gly | Leu | |
| | | | 100 | | | | | 105 | | | | | 110 | | | |
| caa | ggt | aag | tat | ggc | aaa | aca | ggc | tca | gca | ggt | gcc | aga | ggc | cac | act | 384 |
| Gln | Gly | Lys | Tyr | Gly | Lys | Thr | Gly | Ser | Ala | Gly | Ala | Arg | Gly | His | Thr | |
| | 115 | | | | | 120 | | | | | 125 | | | | | |
| ggt | cca | aaa | ggt | caa | aag | ggc | tcc | atg | ggt | gcc | cct | ggt | gag | aga | tgc | 432 |
| Gly | Pro | Lys | Gly | Gln | Lys | Gly | Ser | Met | Gly | Ala | Pro | Gly | Glu | Arg | Cys | |
| 130 | | | | | 135 | | | | | 140 | | | | | | |
| aag | tcc | cac | tac | gcc | gcc | ttt | tct | gtt | ggc | aga | aag | aag | cca | atg | cac | 480 |
| Lys | Ser | His | Tyr | Ala | Ala | Phe | Ser | Val | Gly | Arg | Lys | Lys | Pro | Met | His | |
| 145 | | | | | 150 | | | | | 155 | | | | | 160 | |
| tcc | aac | cac | tac | tac | caa | act | gtt | atc | ttc | gac | act | gag | ttc | gtt | aac | 528 |
| Ser | Asn | His | Tyr | Tyr | Gln | Thr | Val | Ile | Phe | Asp | Thr | Glu | Phe | Val | Asn | |
| | | | | 165 | | | | | 170 | | | | | 175 | | |
| ttg | tac | gac | cac | ttc | aac | atg | ttc | acc | ggc | aag | ttc | tac | tgc | tac | gtt | 576 |
| Leu | Tyr | Asp | His | Phe | Asn | Met | Phe | Thr | Gly | Lys | Phe | Tyr | Cys | Tyr | Val | |
| | | | 180 | | | | | 185 | | | | | 190 | | | |
| cca | ggc | ttg | tac | ttc | ttc | tct | ttg | aac | gtt | cac | acc | tgg | aac | caa | aag | 624 |
| Pro | Gly | Leu | Tyr | Phe | Phe | Ser | Leu | Asn | Val | His | Thr | Trp | Asn | Gln | Lys | |
| | 195 | | | | | 200 | | | | | 205 | | | | | |
| gag | acc | tac | ctg | cac | atc | atg | aag | aac | gag | gag | gag | gtt | gtt | atc | ttg | 672 |
| Glu | Thr | Tyr | Leu | His | Ile | Met | Lys | Asn | Glu | Glu | Glu | Val | Val | Ile | Leu | |
| 210 | | | | | 215 | | | | | 220 | | | | | | |
| ttc | gct | caa | gtt | ggc | gac | aga | tct | atc | atg | caa | tct | caa | tct | ttg | atg | 720 |
| Phe | Ala | Gln | Val | Gly | Asp | Arg | Ser | Ile | Met | Gln | Ser | Gln | Ser | Leu | Met | |
| 225 | | | | | 230 | | | | | 235 | | | | | 240 | |

```
ctt gag ttg aga gag caa gac caa gtt tgg gtt aga ttg tac aag ggc     768
Leu Glu Leu Arg Glu Gln Asp Gln Val Trp Val Arg Leu Tyr Lys Gly
                245                 250                 255 gaa cgt gag aac gcc atc ttc tct gag gag ttg gac acc tac atc acc     816
Glu Arg Glu Asn Ala Ile Phe Ser Glu Glu Leu Asp Thr Tyr Ile Thr
            260                 265                 270 ttc tct ggc tac ttg gtc aag cac gcc acc gag cca tag                 855
Phe Ser Gly Tyr Leu Val Lys His Ala Thr Glu Pro *
            275                 280

<210> SEQ ID NO 40
<211> LENGTH: 284
<212> TYPE: PRT
<213> ORGANISM: Artificial Sequence
<220> FEATURE:
<223> OTHER INFORMATION: b-glucanase::zsig37 full nucleotide sequence
      (pSDH160)

<400> SEQUENCE: 40

Met Lys Phe Ser Leu Ser Thr Leu Thr Val Ile Thr Thr Leu Leu Ser
 1               5                  10                  15

Leu Val Ser Ala Ala Pro Leu Thr Leu Lys Lys Arg Arg Val Pro His
                20                  25                  30

Val Gln Gly Glu Gln Glu Trp Glu Gly Thr Glu Glu Leu Pro Ser
            35                  40                  45

Pro Pro Asp His Ala Glu Arg Ala Glu Gln His Glu Lys Tyr Arg
        50                  55                  60

Pro Ser Gln Asp Gln Gly Leu Pro Ala Ser Arg Cys Leu Arg Cys Cys
65                  70                  75                  80

Asp Pro Gly Thr Ser Met Tyr Pro Ala Thr Ala Val Pro Gln Ile Asn
                85                  90                  95

Ile Thr Ile Leu Lys Gly Glu Lys Gly Asp Arg Gly Asp Arg Gly Leu
                100                 105                 110

Gln Gly Lys Tyr Gly Lys Thr Gly Ser Ala Gly Ala Arg Gly His Thr
            115                 120                 125

Gly Pro Lys Gly Gln Lys Gly Ser Met Gly Ala Pro Gly Glu Arg Cys
130                 135                 140

Lys Ser His Tyr Ala Ala Phe Ser Val Gly Arg Lys Lys Pro Met His
145                 150                 155                 160

Ser Asn His Tyr Tyr Gln Thr Val Ile Phe Asp Thr Glu Phe Val Asn
                165                 170                 175

Leu Tyr Asp His Phe Asn Met Phe Thr Gly Lys Phe Tyr Cys Tyr Val
            180                 185                 190

Pro Gly Leu Tyr Phe Phe Ser Leu Asn Val His Thr Trp Asn Gln Lys
        195                 200                 205

Glu Thr Tyr Leu His Ile Met Lys Asn Glu Glu Val Val Ile Leu
    210                 215                 220

Phe Ala Gln Val Gly Asp Arg Ser Ile Met Gln Ser Gln Ser Leu Met
225                 230                 235                 240

Leu Glu Leu Arg Glu Gln Asp Gln Val Trp Val Arg Leu Tyr Lys Gly
                245                 250                 255

Glu Arg Glu Asn Ala Ile Phe Ser Glu Glu Leu Asp Thr Tyr Ile Thr
            260                 265                 270

Phe Ser Gly Tyr Leu Val Lys His Ala Thr Glu Pro
        275                 280
```